United States Patent [19]

Katoh et al.

[11] Patent Number: 5,091,311
[45] Date of Patent: Feb. 25, 1992

[54] **THE PRODUCTION OF KSB-1939 MACROLIDES USING *STREPTOMYCES HYGROSCOPICUS***

[75] Inventors: Hideki Katoh, Kakegawa; Reisuke Kobayashi, Shizuoka; Tomonori Shimazu, Hamamatsu; Akinori Suzuki; Akira Isogai, both of Chiba; Osamu Tada, Shizuoka, all of Japan

[73] Assignee: Kumiai Chemical Industry Co., Ltd., Tokyo, Japan

[21] Appl. No.: 512,126

[22] Filed: Apr. 17, 1990

Related U.S. Application Data

[62] Division of Ser. No. 216,128, Jul. 7, 1988, Pat. No. 4,939,166.

[30] Foreign Application Priority Data

Jul. 7, 1987 [JP] Japan .................. 62-169447
Jul. 23, 1987 [JP] Japan .................. 62-184621
Feb. 2, 1988 [JP] Japan .................. 63-22543

[51] Int. Cl.$^5$ .................................... C12R 1/465
[52] U.S. Cl. ........................... 435/119; 514/450
[58] Field of Search .................. 514/450; 435/119

[56] References Cited

U.S. PATENT DOCUMENTS

| | | | |
|---|---|---|---|
| 4,390,546 | 6/1983 | Goetz et al. | 424/279 |
| 4,415,669 | 11/1983 | Hernandez | 424/253 |
| 4,457,920 | 7/1984 | Mrozik | 424/180 |
| 4,939,166 | 7/1990 | Katoh et al. | 514/450 |

FOREIGN PATENT DOCUMENTS

| | | |
|---|---|---|
| 074758 | 3/1983 | European Pat. Off. |
| 237341 | 9/1987 | European Pat. Off. |
| 254583 | 1/1988 | European Pat. Off. |
| 274871 | 7/1988 | European Pat. Off. |

*Primary Examiner*—Douglas W. Robinson
*Assistant Examiner*—S. Saucier
*Attorney, Agent, or Firm*—Oblon, Spivak, McClelland, Maier & Neustadt

[57] ABSTRACT

A method of producing novel macrolides of the formula

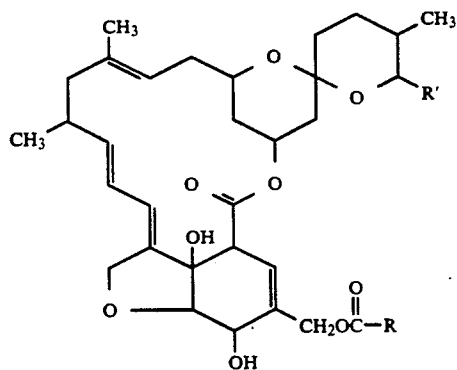

wherein R means

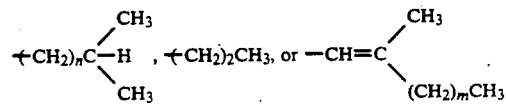

in which n stands for an integer of 0–2 and m denotes an integer of 0 or 1, and R' denotes a methyl or ethyl group using *Streptomyces hygroscopicus* is described.

13 Claims, 21 Drawing Sheets

THE PRODUCTION OF KSB-1939 MACROLIDES USING STREPTOMYCES HYGROSCOPICUS

This is a division of application Ser. No. 216,128, filed July 7, 1988, now U.S. Pat. No. 4,939,166.

BACKGROUND OF THE INVENTION

1) Field of the Invention

This invention relates to novel physiologically-active compounds exhibiting pesticidal effects including insecticidal, acaricidal, nematocidal and anthelmintic effects and also to production processes thereof.

2) Description of the Related Art

Needless to say, agrochemicals are indispensable for stably maintaining high agricultural harvest. It is however not possible to deny the possibility that they may remain in crops and may develop problems such as toxic hazard to human bodies and environmental contamination. There is hence a demand for the development of agrochemicals having still higher safety. With a view toward developing still safer agrochemicals, the present inventors have carried out an investigation while paying attention to pesticidal products.

As insecticidal substances available from microorganisms, there have been known cyclic peptides led by destruxin produced by a mold fungus, [Agricultural Biological Chemistry, 26, 36 (1962)]; crystalline proteins such as δ-endotoxin produced by a bacterium of Bacillus [Annual Review of Entomology, 12, 289 (1967)]; pyrones such as piericidin produced by an actinomycete [Agricultural Biological Chemistry, 30, 517 (1966)]; macrolide substances represented by tetranactin classified under the group of electron transport inhibitors, macrotetrolides, containing pyrrolidone as a nucleus [The Journal of Antibiotics, 24A, 418 (1971)], milbemycin having a structure similar to the compounds of this invention [Japanese Pat. Laid-Open No. 32481/1981; U.S. Pat. No. 4,346,171], avermectin [U.S. Pat. No. 4,199,569]; etc.

SUMMARY OF THE INVENTION

In order to obtain other novel substances produced by microorganisms and having physiological activities, the present inventors isolated microorganisms from a variety of soils and have proceeded further with an investigation on metabolic products produced by the microorganisms. As a result, it has been found that an active substance capable of showing strong pesticidal effects such as insecticidal, acaricidal, nematocidal and anthelmintic effects is produced in a culture of KSB-1939 strain isolated newly from some of the soils. It has now been succeeded in isolating and collecting the effective substance.

In one aspect of this invention, there is thus provided a KSB-1939 compound represented by the following general formula (I):

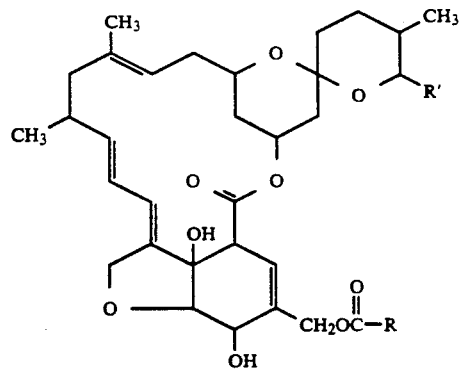

wherein R means

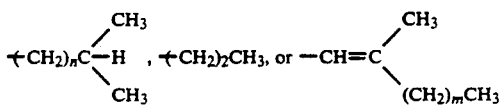

in which n stands for an integer of 0-2 and m denotes an integer of 0 or 1, and R' denotes a methyl or ethyl group.

In another aspect of this invention, there is also provided a process for the production of the KSB-1939 compound represented by the general formula (I), which comprises culturing a KSB-1939 compound producing strain of Streptomyces and then collecting the KSB-1939 compound from the resultant culture.

In a further aspect of this invention, there is also provided a pesticidal agent which comprises, as an effective ingredient, the KSB-1939 compound represented by the general formula (I).

The compounds according to this invention have insecticidal and acaricidal effects and anthelmintic activities against animal parasites.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
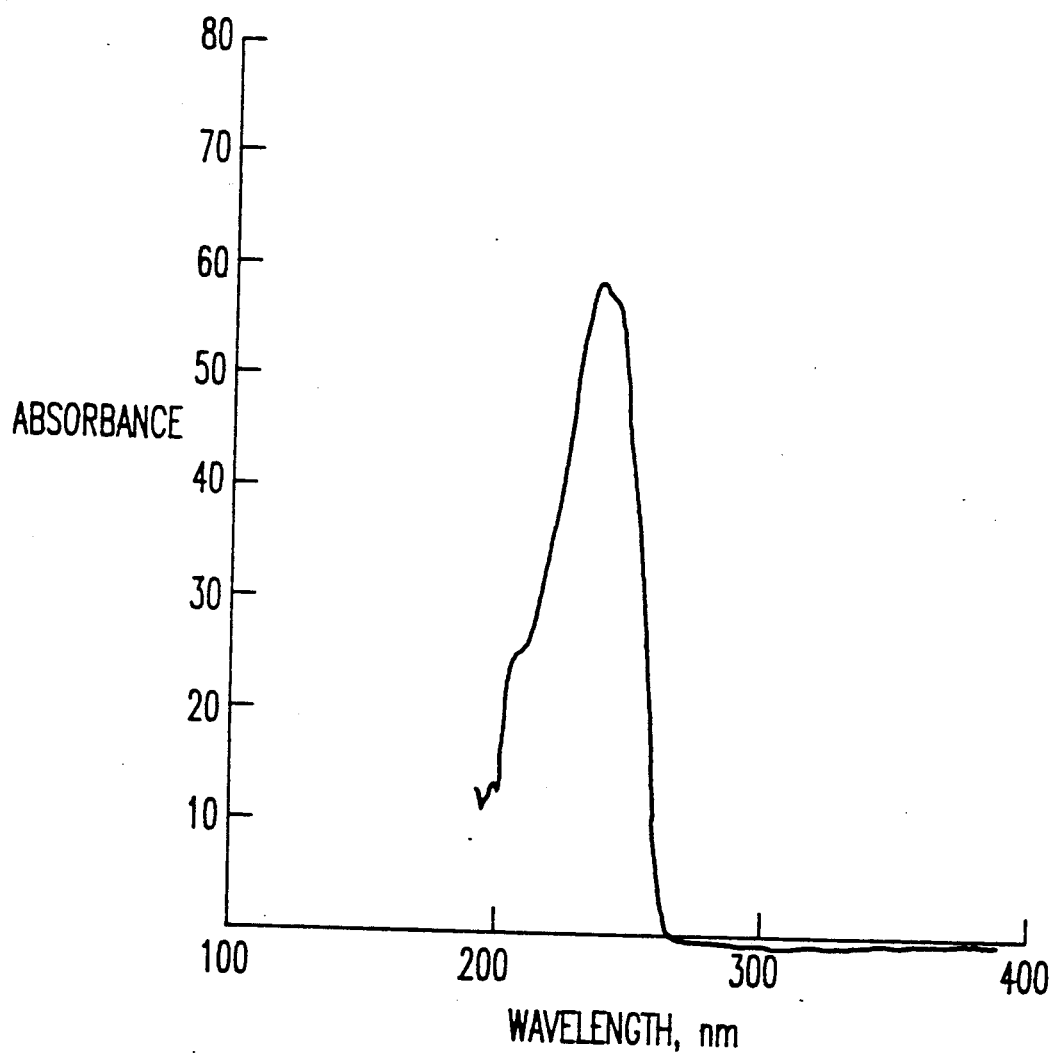
FIG. 1 shows an ultraviolet absorption spectrum of KSB-1939H$_2$, FIG. 2 an infrared absorption spectrum of KSB-1939H$_2$, and FIG. 3 an nuclear magnetic resonance spectrum of KSB-1939H$_2$.

Seven types of KSB-1939 compounds are included in the present invention, owing to different combinations of R and R' in the general formula (I). As will be described subsequently, these compounds are obtained as a mixture by culturing a KSB-1939 producing bacterium. This mixture will hereinafter be called "KSB-1939 substance" and a bacterium strain capable of producing KSB-1939 substance will hereinafter be called "KSB-1939 substance producing strain".

KSB-1939 substance of this invention is obtained by culturing a KSB-1939 substance producing strain of Streptomyces, isolating an active fraction from the culture and then purifying same. As one example of KSB-1939 substance producing strains, there is an actinomycete, KSB-1939 strain, isolated from soil of Shingu-shi, Wakayama-ken, Japan. The followings are microbiological characteristics of KSB-1939 strain.

The identification of the above strain was conducted by the method of the International Streptomyces Plan (ISP) and the Waksman's method, while its description was made by following examples of the ISP.

(1) Morphological characteristics

Substrate mycelia grow while branching. Splitting of mycelia is not observed. Aerial mycelia briskly adhere to glucose-asparagine agar medium, oatmeal agar medium and the like, and sporulation is also good. Aerial mycelia extend into the air while branching. Aerial spore chains occur by monopodial branching on short main axes and branches. Aerial spore chains are usually in the form of a coil-like spiral. When cultured for a long period of time, tips of spore chains turn to black and sticky balls. At areas where the above turning to black and sticky balls have proceeded further, aerial hyphae are converted in their entirety into dark brown and sticky balls (or glucose-asparagine agar medium, oatmeal agar medium). The widths of spore chains range from 0.5 to 0.8 micrometers, and spore surfaces present warty appearance. Since the discreteness of spores is not clear, the detailed shape and connected number of individual spores are unknown but the connection of 10 or more spores is observed. Further, spores do not show mobility, and sporangia, sclerotia and the like are not observed.

(2) Analysis of diaminopimelic acid

LL-diaminopimelic acid is recognized from an analysis of a whole cell hydrolysate, so that the above strain has cell wall Type-I.

(3) Cultural characteristics on various media

The cultural characteristics in the third week of cultivation are summarized in Table 1.

TABLE 1

| Medium | Aerial mycelium color | Reverse color | Soluble pigment |
|---|---|---|---|
| Sucrose-nitrate agar medium | White-gray series (a) | Pale yellow | None |
| Glucose-asparagine agar medium | White-gray series (4ig) | Pale yellow | Pale yellow |
| Glycerol-asparagine agar medium | White | Pale yellow brown | None |
| Starch agar medium | White-gray series (2fe) | Pale yellow | None |
| Tyrosine agar medium | White-gray series (4li) | Dark yellow orange to yellow brown | Dull yellow |
| Nutrient agar medium | White (1iae-2ap-3cp) | Pale yellow | None |
| Yeast malt medium | Gray series (4ig-4li) | Dark yellow orange | Dark yellow orange to yellow brown |
| Oatmeal agar medium | Gray series (4ig-4li) | Brown gray | None |

(4) Physiological properties

| | |
|---|---|
| (i) Growth temperature range: | 20–40° C. |
| Optimum temperature range: | 25–35° C. |
| (ii) Liquefaction of gelatin: | + |
| (iii) Hydrolysis of starch: | + |
| (iv) Coagulation of skim milk: | + |
| Peptonization of skim milk: | + |
| (v) Reduction of melanin-like pigments: | |
| Tyrosine agar medium | − |
| Peptone-yeast-iron agar medium | − |
| Trypsine-yeast broth | − |
| (vi) Nitrate reduction: | + |

(5) Utilization of individual carbon sources (on Plydham-Goldlieb agar medium)

Utilize all carbon sources of L-arabinose, D-xylose, D-glucose, D-fractose, sucrose, L-rhamnose, raffinose, D-mannitol and I-inositol.

With reference to International Journal of Systematic Bacteriology, 22, 307–311 (1972), identification was carried out on the basis of the above-described mycological properties. Fundamental properties (the shape and the state of growth on various media) of KSB-1939 strain were found to conform well with those of *Streptomyces hygroscopicus* although slight differences were observed in the utilization of sucrose and raffinose. The present inventors therefore named the above strain as *Streptomyces hygroscopicus* KSB-1939" and deposited it under FERM BP-1901 on June 25, 1987. Incidentally, KSB-1939 strain is susceptible to variations in properties as observed with the other actinomycetes. It is possible to use not only KSB-1939 strain but also mutants (both spontaneous and inductive mutants), transformants and recombinants derived from the strain in the present invention, so long as they produce KSB-1939 compounds and their character sources are dependent on KSB-1939 strain.

A medium containing nutrients, which general microorganisms can assimilate, may be used upon culture of KSB-1939 strain. As nutrient sources, known nutrient sources which have been used for the culture of actinomycetes can be used. For example, glucose, glycerin, maltose, lactose, starch syrup, dextrin, starch, molasses, animal and plant oils, etc. may be used as carbon sources. As usable nitrogen sources, may be mentioned dry yeasts, soybean meal, wheat germ, corn steep liquor, peanut flour, cotton seed flour, peptone, meat extract, yeast extract, ammonium sulfate, sodium nitrate, urea, and the like. In addition, sodium, potassium, calcium, magnesium, cobalt, chlorine, phosphoric acid and/or other ion-forming inorganic salts may also be added effectively as needed. It is also possible to suitably add one or more of such organic and inorganic materials that may promote the growth of microorganisms and accelerate the production of KSB-1939 substance. As a culturing method, culture under aerobic conditions, especially, submerged tank culture is most suitable. Although the suitable culture temperature ranges from 15° C. to 37° C., culturing may be conducted around 26°-30° C. in many instances. The production of KSB-1939 substance generally reaches the maximum in 5-10 days for both shake culture and tank culture, subject to variations depending on the culture and culture conditions.

KSB-1939 substance thus produced can be extracted and purified from the culture, relying upon its physicochemical properties. In particular, they can be efficiently extracted and purified in accordance with the following procedure.

Since most of KSB-1939 substance is produced in cultured cells, the culture is subjected to filtration or centrifugation to collect cells. The cells are extracted with acetone or an alcohol. After concentrating the extract under reduced pressure, the concentrate is extracted in a solvent such as ethyl acetate or chloroform. As an alternative, the culture or concentrate is extracted directly with a solvent such as that mentioned above. Upon concentration of the resultant solution to dryness, a powdery or oily crude product containing KSB-1939 substance can be obtained.

KSB-1939 substance thus obtained have the following characteristics.

(1) Their constituent elements are carbon, hydrogen and oxygen, and nitrogen is not contained.

(2) Characteristic absorption occurs at 238-242 nm in an ultraviolet absorption spectrum.

(3) Characteristic absorption caused by a carbonyl group appear at 1720-1740 cm$^{-1}$ in an infrared absorption spectrum.

(4) A peak attributed to ion fragments appears at a molecular weight of either 526 or 540 in an EI (electron impact) mass spectrum.

(5) Two characteristic peaks corresponding to a hydroxymethyl group occur at 4.6 ppm and 4.8 ppm respectively in a $^1$H-NMR (hydrogen nuclear magnetic resonance) spectrum.

(6) A specific peak corresponding to the methylene carbon of a hydroxymethyl group appears at a position of 63-65 ppm in a $^{13}$C-NMR (carbon nuclear magnetic resonance) spectrum.

(7) Two characteristic peaks caused by a carbonyl group appear at a position of 160-180 ppm in a $^{13}$C-NMR (carbon nuclear magnetic resonance) spectrum.

Namely, KSB-1939 substance is a macrolide substance called "16-membered cyclic macloride" and has characteristic absorption caused by the macrolide ring appears at 238-242 nm in an ultraviolet absorption spectrum. Further, specific absorption attributable to a carbonyl group occurs at 1720-1740 cm$^{-1}$ in an infrared absorption spectrum. It is a further characteristic of KSB-1939 substance that it contains an alkanoyloxymethyl or alkenoyloxymethyl group in the C4 side chain. Namely, it does not contain the nitrogen element which constitutes the pyrrole ring as seen in milbemycin $C_1$, $C_2$ and F. Furthermore, it has two hydroxymethyl-related characteristic peaks at 4.6 ppm and 4.8 ppm in a $^1$H-NMR (hydrogen nuclear magnetic resonance) spectrum and also a characteristic peak of the methylene carbon of the hydroxymethyl group at the position of 65-65 ppm in a $^{13}$C-NMR (carbon nuclear magnetic resonance) spectrum. Owing to the carbonyl carbons of the carbonyl group and macrolide ring contained commonly in the C4 side chain, two characteristic peaks appear at the position of 160-180 ppm in a $^{13}$C-NMR (carbon nuclear magnetic resonance) spectrum. On the other hand, a characteristic peak corresponding to a side chain separated by a rearrangement shift appears at the molecular weight of 526 or 540 owing to ion fragments in an EI-MASS spectrum.

The above KSB-1939 substance is not a single compound but contains the following 7 compounds which are represented by different combinations of R and R' in the general formula (I).

TABLE 2

| Compound Name | General formula (I) R | R' |
|---|---|---|
| KSB-1939H$_2$ | $-CH=C\begin{smallmatrix}CH_3\\CH_3\end{smallmatrix}$ | Methyl |
| KSB-1939H$_3$ | $-CH_2-C\begin{smallmatrix}CH_3\\H\\CH_3\end{smallmatrix}$ | Methyl |
| KSB-1939H$_4$ | $-CH=C\begin{smallmatrix}CH_3\\C_2H_5\end{smallmatrix}$ | Methyl |
| KSB-1939H$_5$ | $-CH_2-CH_2-C\begin{smallmatrix}CH_3\\H\\CH_3\end{smallmatrix}$ | Methyl |
| KSB-1939S$_5$ | $-CH=C\begin{smallmatrix}CH_3\\CH_3\end{smallmatrix}$ | Ethyl |
| KSB-1939L$_{3\alpha}$ | $-C\begin{smallmatrix}CH_3\\H\\CH_3\end{smallmatrix}$ | Methyl |
| KSB-1939L$_{3\beta}$ | $-CH_2-CH_2-CH_3$ | Methyl |

Among these compounds, KSB-1939H$_4$ includes stereoisomers of cis-isomer (Z-form) and trans-isomer (E-form) with respect to the double bond of the group R and is separated into KSB-1939H$_{4Z}$ and KSB-1939H$_{4E}$. However, most of KSB-1939H$_4$ is E form.

Among these compounds, most preferred are those represented by the general formula (I) in which R is

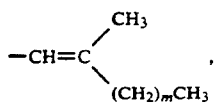

m being an integer of 0 or 1.

In order to obtain the individual compounds which constitute KSB-1939 substance, it is necessary to fractionate and purify KSB-1939 substance by a known method employed routinely for the purification of fat-soluble substances, for example, column chromatography on a carrier such as silica gel or alumina. KSB-1939 substance according to this invention can be obtained in a high yield and with a high purity by choosing conditions for the chromatography. In order to obtain a still-purified product, high-performance liquid chromatography of the purified product making use of a normal phase column or reversed phase column is effective. In the chromatography of the normal phase system, the constituent compounds of KSB-1939 substance are eluted generally in the order of KSB-1939H$_4$ (Z-form), H$_4$ (E-form), H$_2$, H$_3$-H$_5$ mixture, S$_5$, L$_{3\alpha}$ and L$_{3\beta}$. In the chromatography of the reversed phase system, the constituent compounds of KSB-1939 substance are fractionated and eluted normally in the order of KSB-1939L$_{3\alpha}$-L$_{3\beta}$ mixture, H$_2$, H$_3$, H$_4$ (Z-form)-H$_4$ (E-form) mixture, S$_5$ and H$_5$. Besides, gel filtration, fractionation making use of an adsorbent, crystallization and the like may also be used.

The constituent compounds of KSB-1939 substance of this invention, which are obtained in the above-described method, have the following physicochemical properties respectively.

Figure 2:
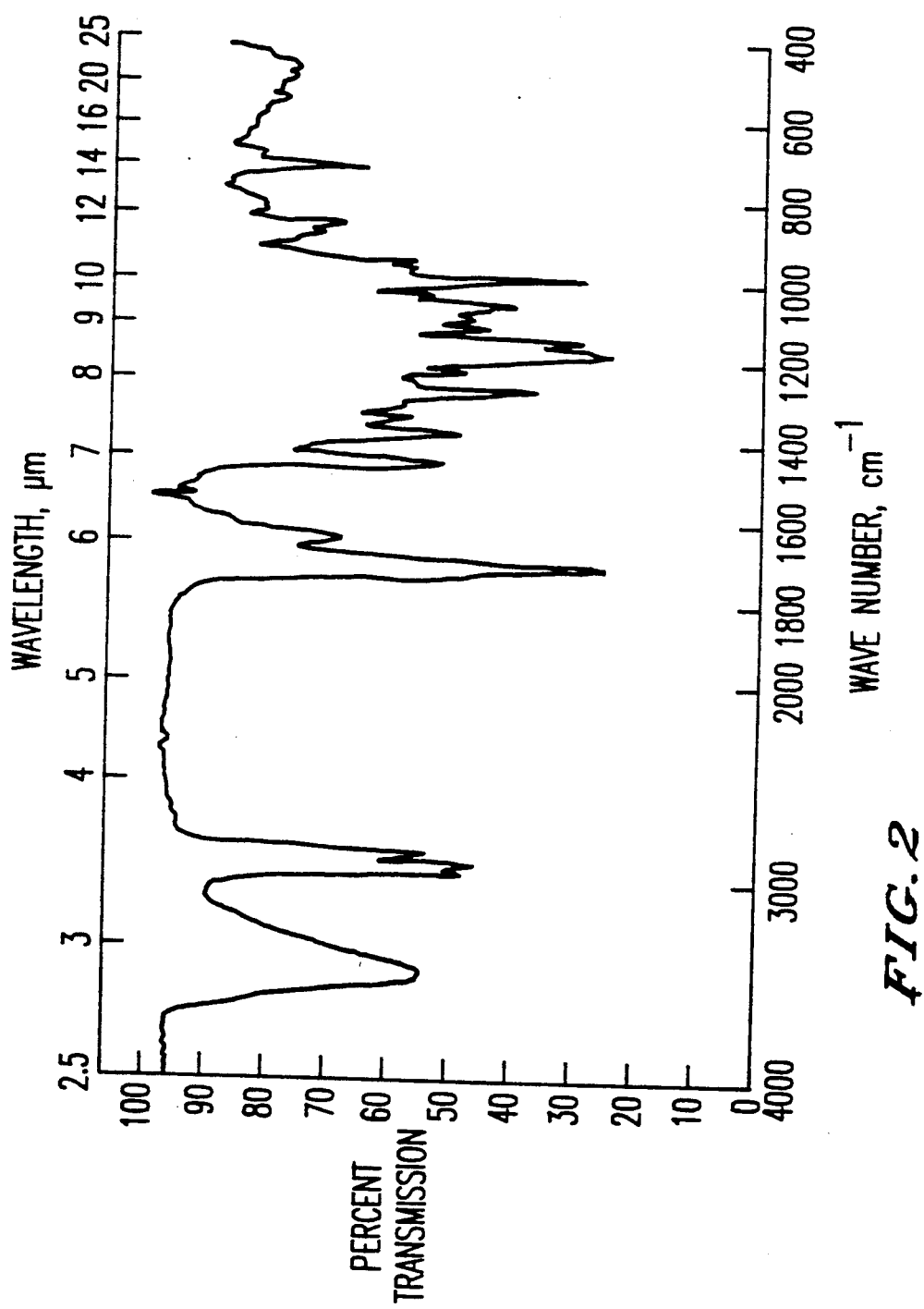
Figure 3:
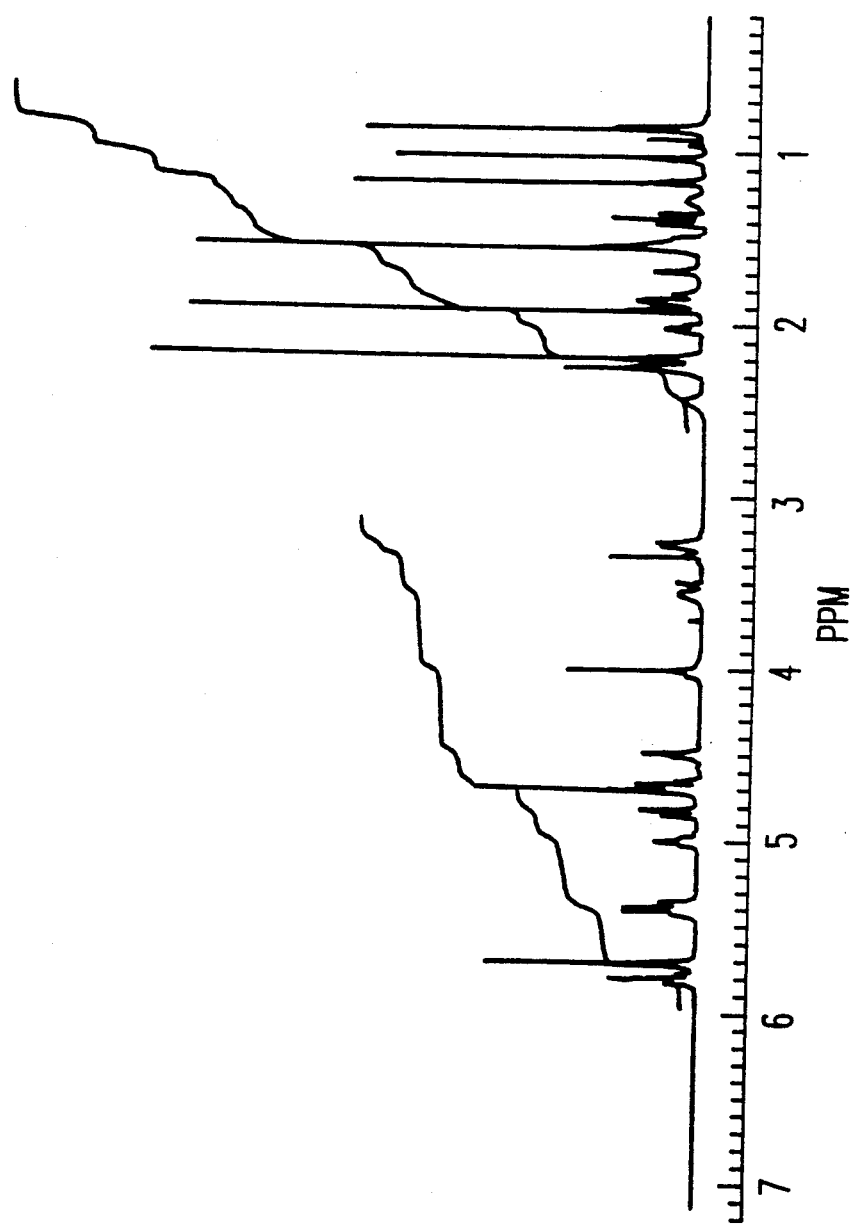

---
KSB-1939H$_2$:

(1) Compound color: Colorless
(2) Elemental analysis data:
　C: 69.01%
　H: 7.99%
　O: 23.00%
(3) Molecular formula: C$_{36}$H$_{50}$O$_9$
(4) Molecular weight: 626 (FDMS)
(5) UV spectrum: Shown in FIG. 1.
(6) IR spectrum: Shown in FIG. 2.
(7) NMR spectrum: Shown in FIG. 3.
(8) Color reactions (on thin silica gel layer):

| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

(9) Solubility:
　Insoluble in water. Soluble in methanol, acetone, ethyl acetate, chloroform and hexane.
(10) Distinction of basic, acidic or neutral: Neutral.

---
KSB-1939H$_3$

Figure 4:
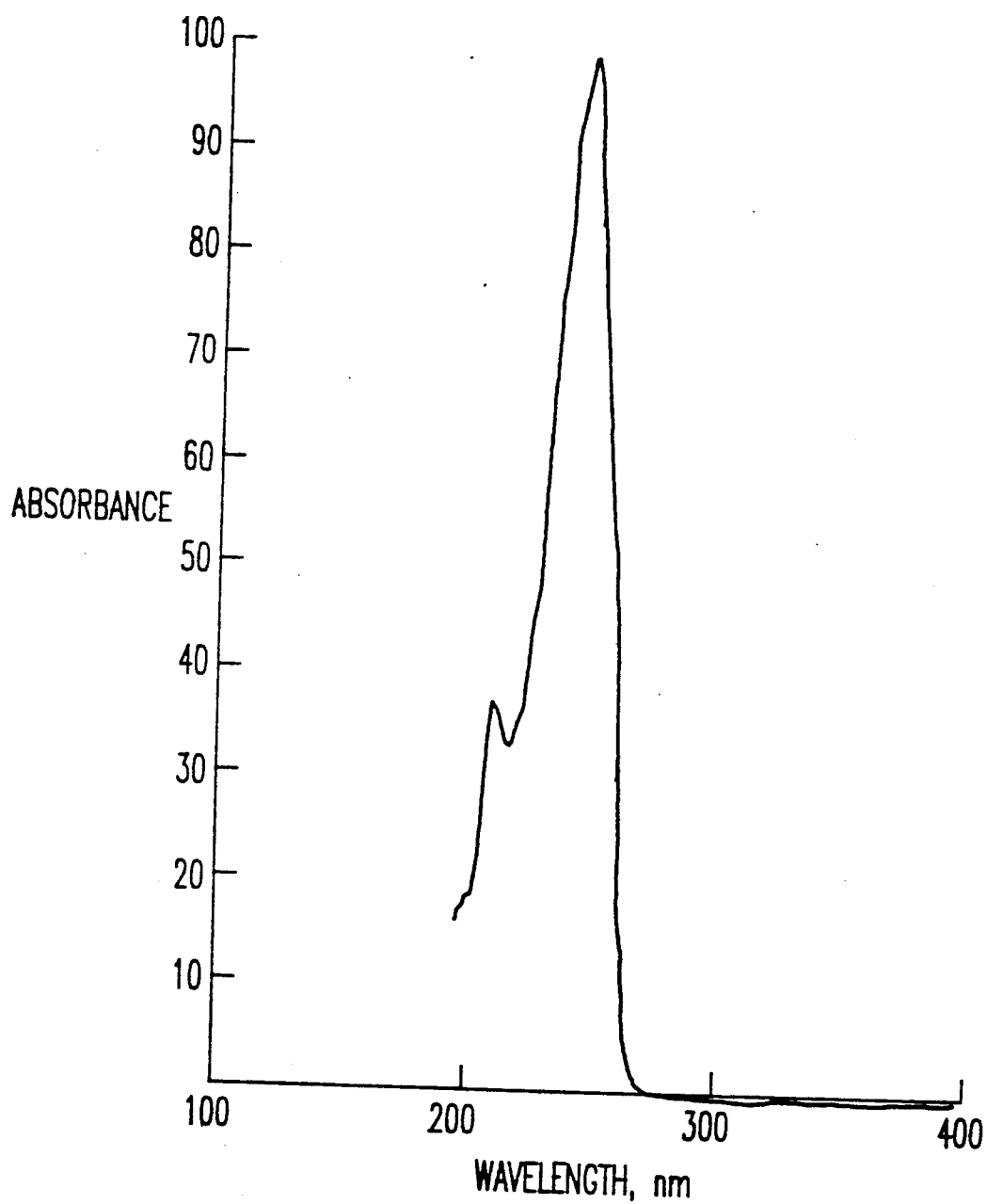
FIG. 4 shows an ultraviolet absorption spectrum of KSB-1939H$_3$, FIG. 5 an infrared absorption spectrum of KSB-1939H$_3$, and FIG. 6 an nuclear magnetic resonance spectrum of KSB-1939H$_3$.
Figure 5:
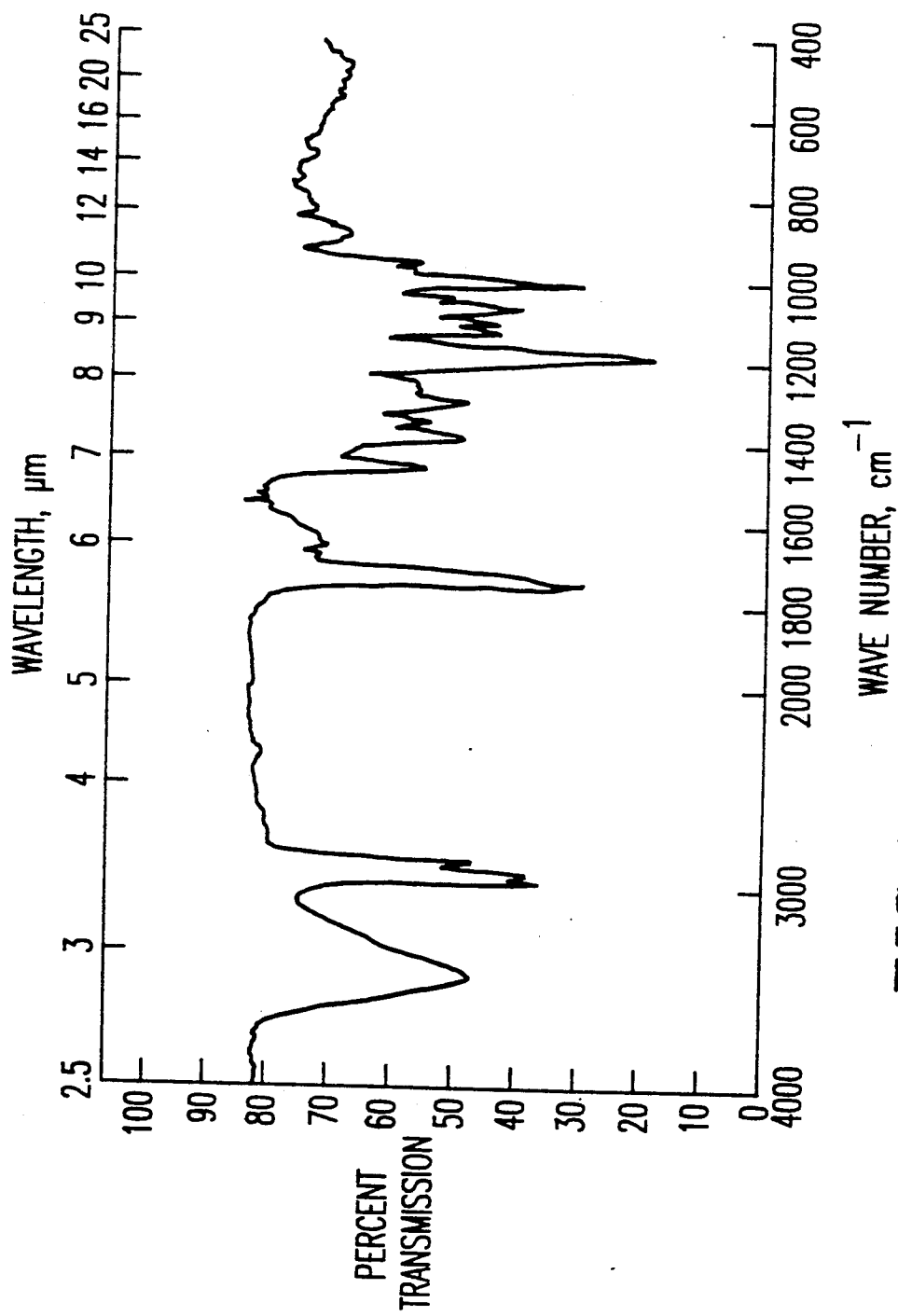
Figure 6:
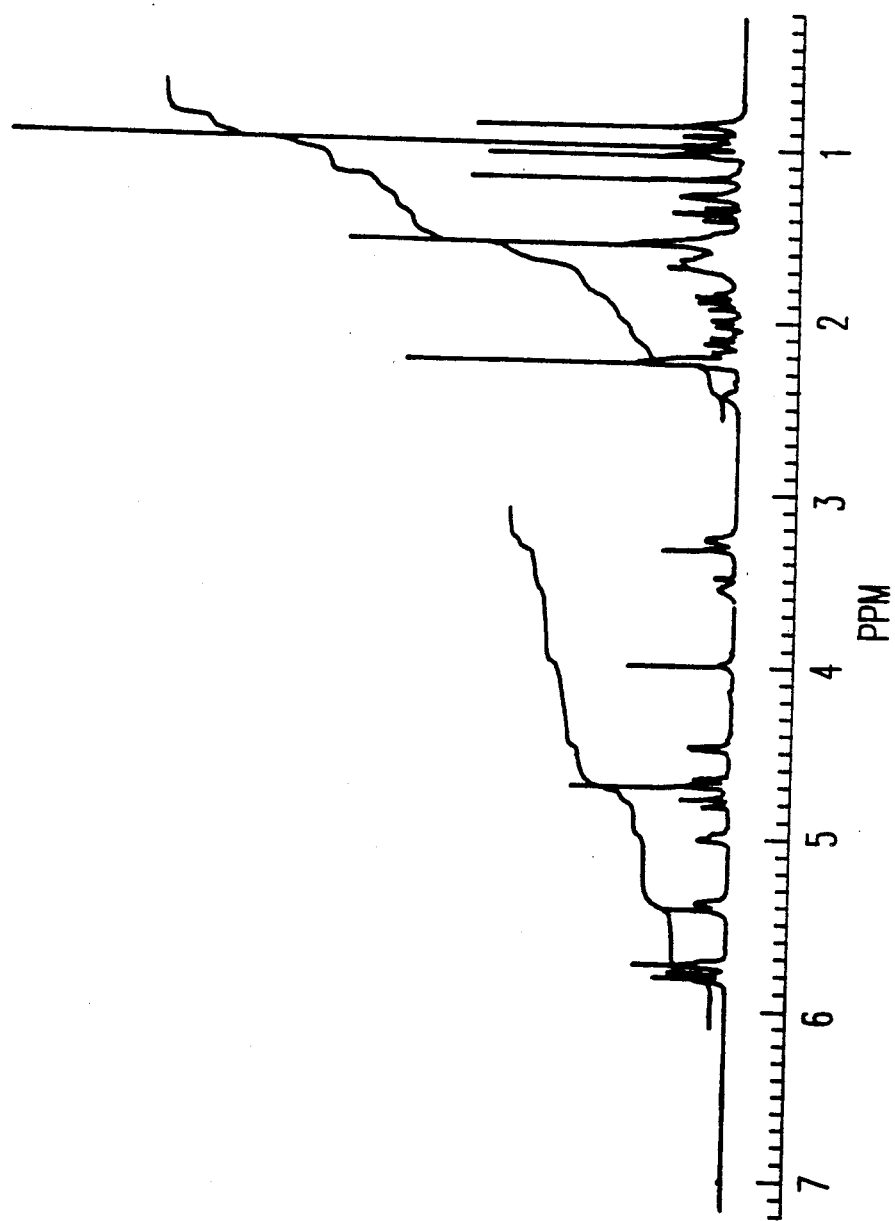

(1) Compound color: Colorless
(2) Elemental analysis data:
　C: 68.79%
　H: 8.28%
　O: 22.93%
(3) Molecular formula: C$_{36}$H$_{52}$O$_9$
(4) Molecular weight: 628 (FDMS)
(5) UV spectrum: Shown in FIG. 4.
(6) IR spectrum: Shown in FIG. 5.
(7) NMR spectrum: Shown in FIG. 6.
(8) Color reactions (on thin silica gel layer):

| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

(9) Solubility:
　Insoluble in water. Soluble in methanol, acetone, ethyl acetate, chloroform and hexane.
(10) Distinction of basic, acidic or neutral: Neutral.

---
KSB-1939H$_4$

Figure 7:
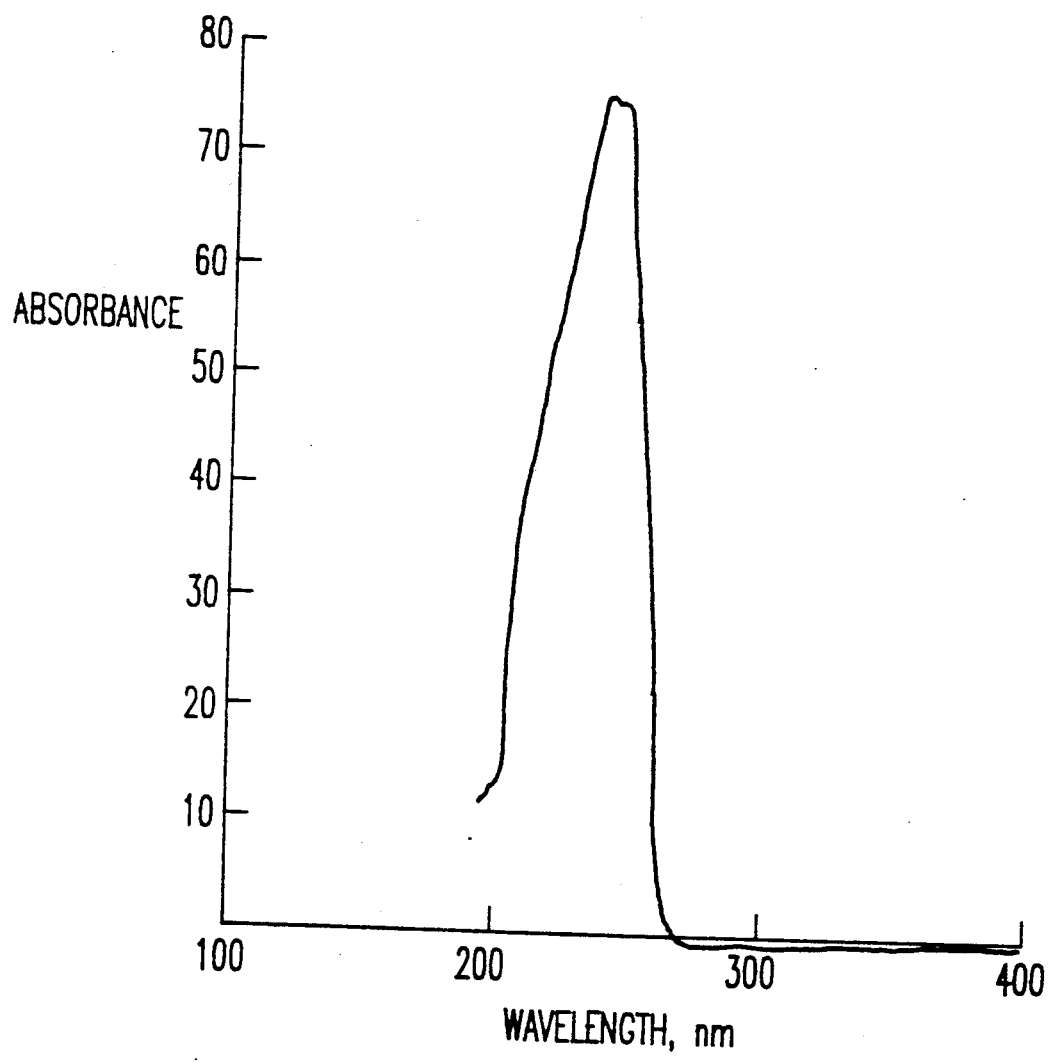
FIG. 7 shows an ultraviolet absorption spectrum of KSB-1939H$_4$, FIG. 8 an infrared absorption spectrum of KSB-1939H$_4$, and FIGS. 9-A and 9-B nuclear magnetic resonance spectra of KSB-1939H$_4$ (E-form) and KSB-1939H$_4$ (Z-form) respectively.
Figure 8:
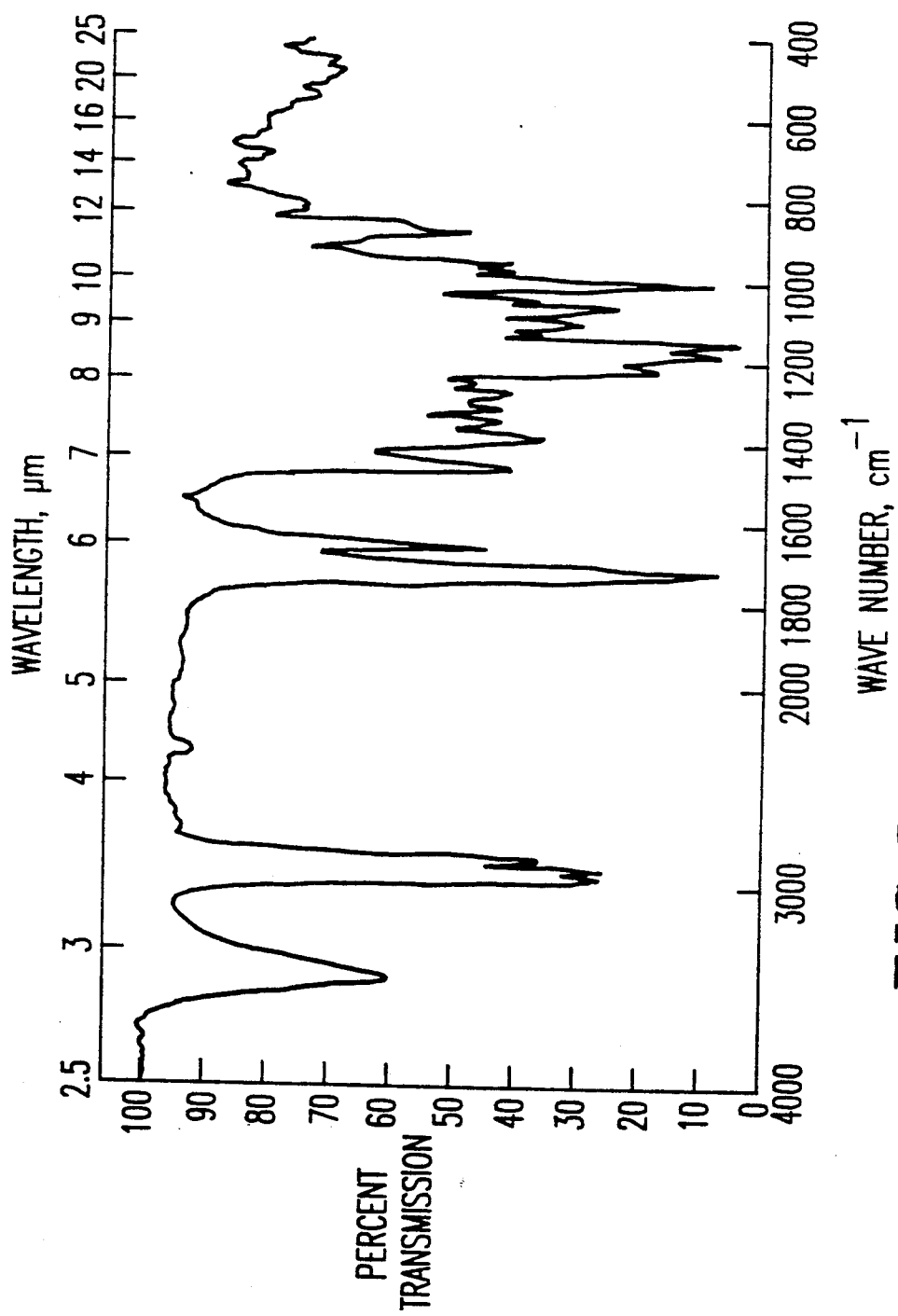
Figure 9A:
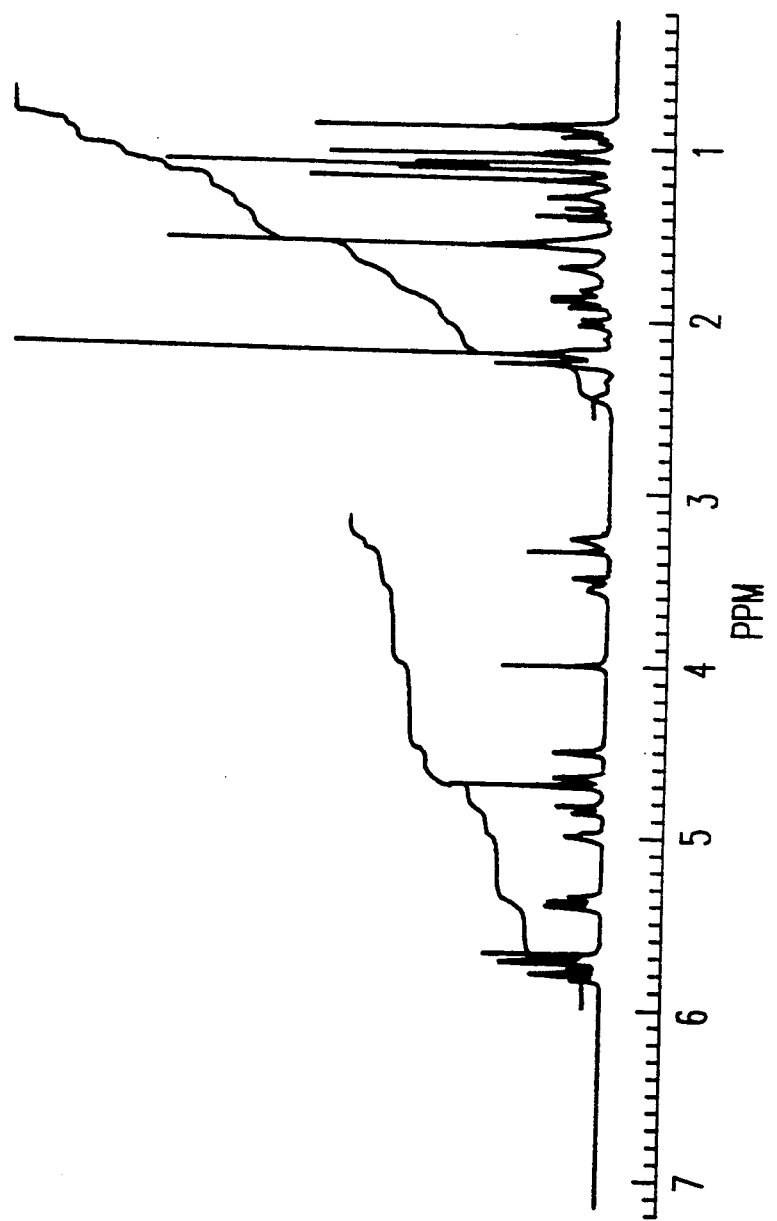
Figure 9B:
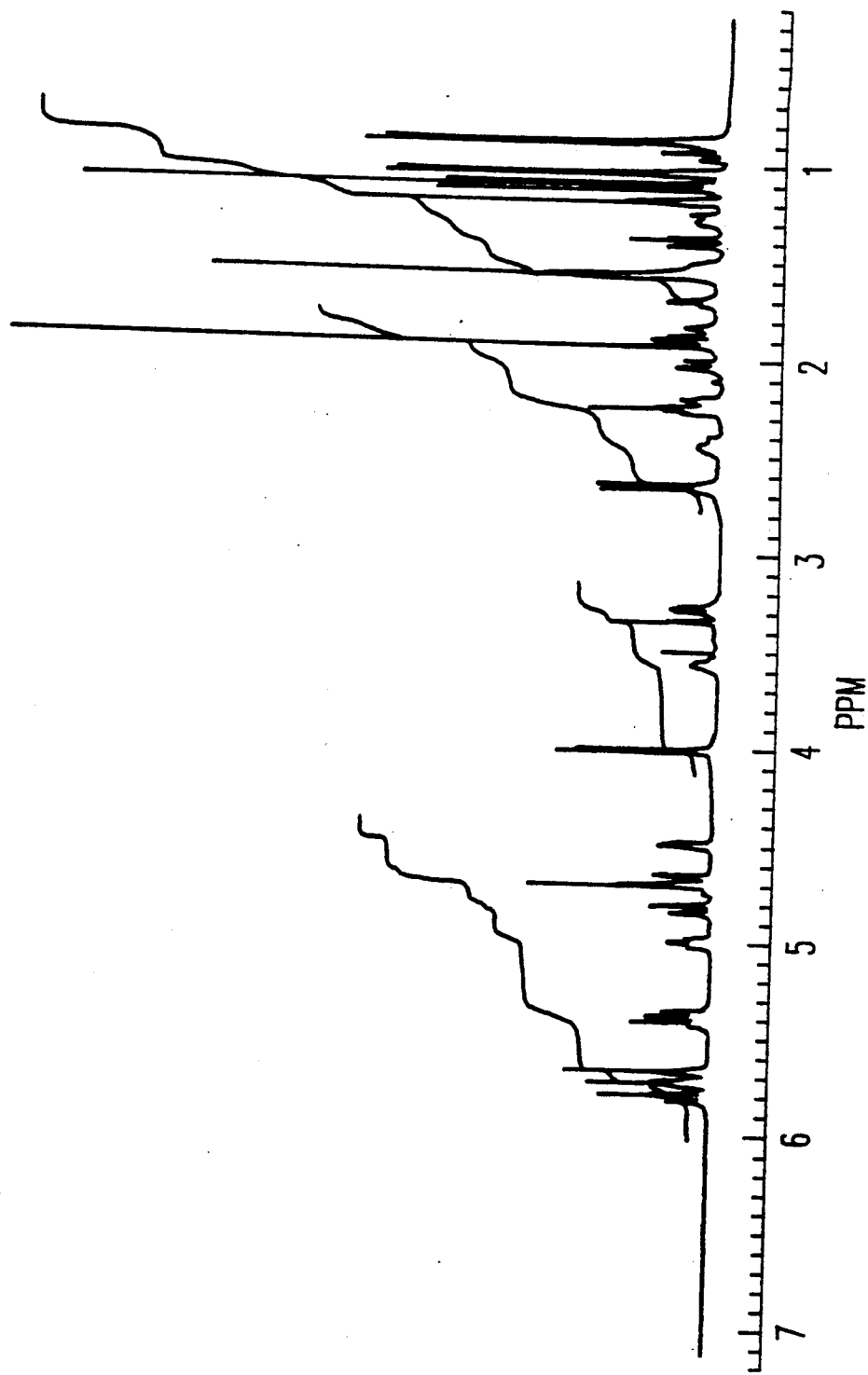

(1) Compound color: Colorless
(2) Elemental analysis data:
　C: 69.38%
　H: 8.12%
　O: 22.50%
(3) Molecular formula: C$_{37}$H$_{52}$O$_9$
(4) Molecular weight: 640 (FDMS)
(5) UV spectrum: Shown in FIG. 7.
(6) IR spectrum: Shown in FIG. 8.
(7) NMR spectrum: Shown in FIGS. 9-A and 9-B.
(8) Color reactions (on thin silica gel layer):

| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

(9) Solubility:
　Insoluble in water. Soluble in methanol, acetone, ethyl acetate, chloroform and hexane.
(10) Distinction of basic, acidic or neutral: Neutral.

---
KSB-1939H$_5$

Figure 10:
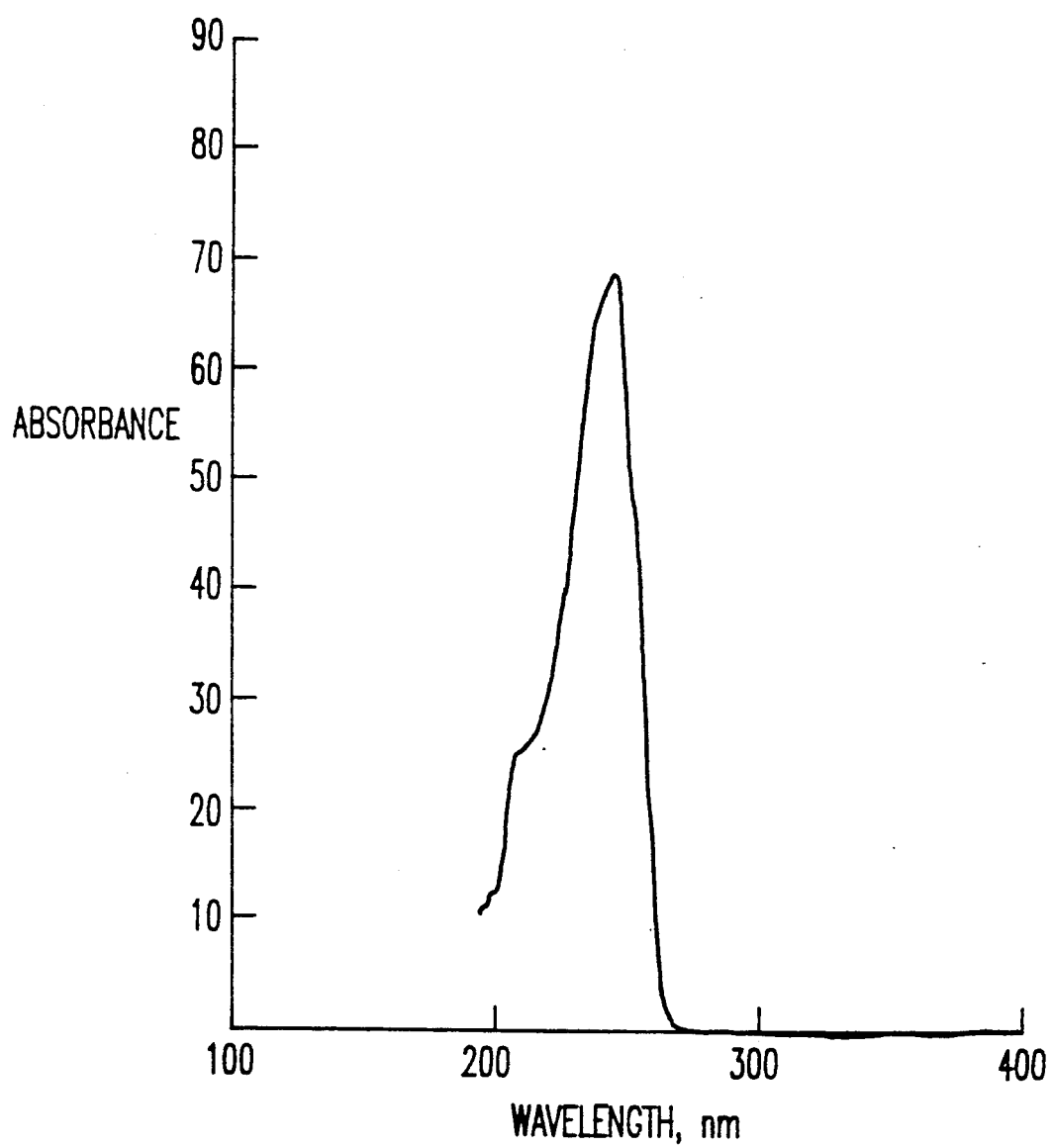
FIG. 10 shows an ultraviolet absorption spectrum of KSB-1939H$_5$, FIG. 11 an infrared absorption spectrum of KSB-1939H$_5$, and FIG. 12 an nuclear magnetic resonance spectrum of KSB-1939H$_5$.
Figure 11:
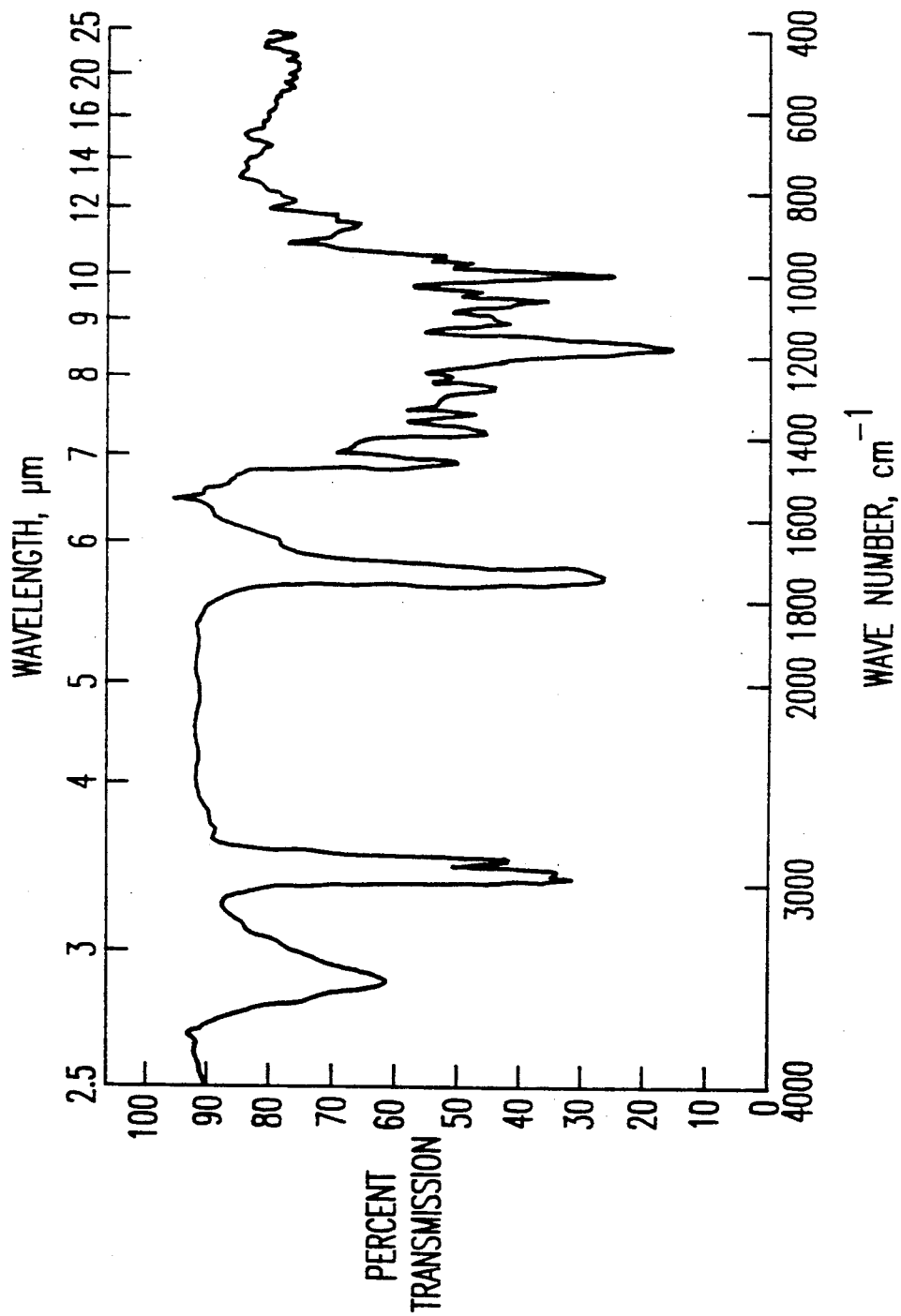
Figure 12:
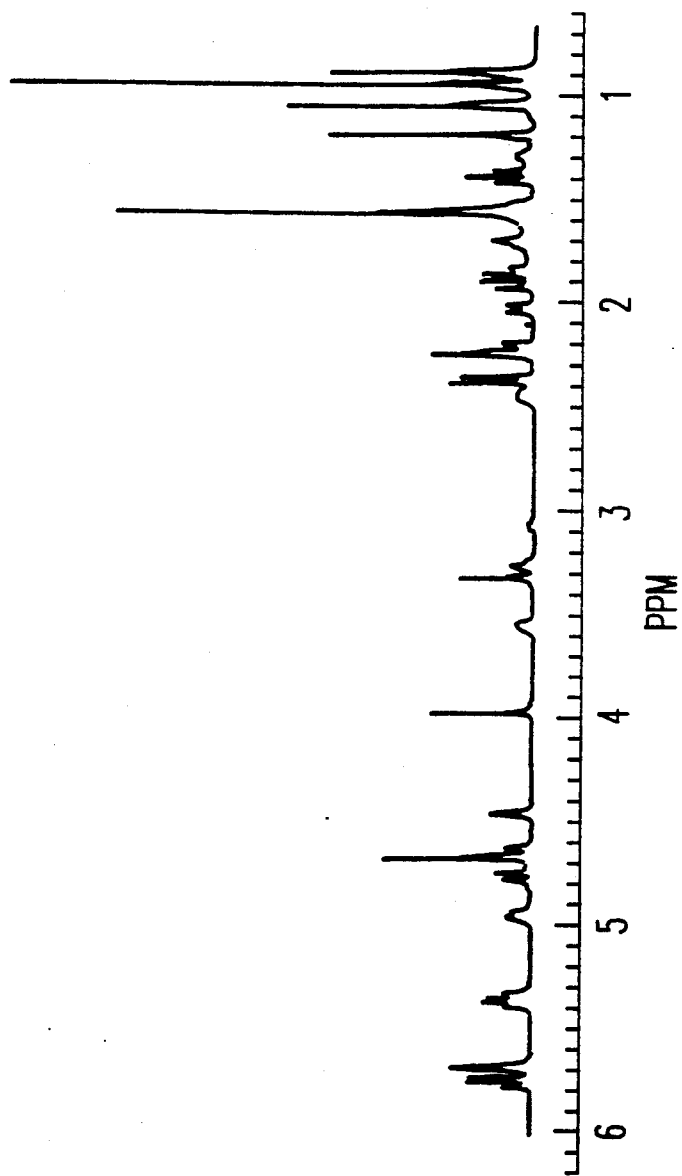

(1) Compound color: Colorless
(2) Elemental analysis data:
　C: 69.16%
　H: 8.41%
　O: 22.43%
(3) Molecular formula: C$_{37}$H$_{54}$O$_9$
(4) Molecular weight: 642 (FDMS)
(5) UV spectrum: Shown in FIG. 10.
(6) IR spectrum: Shown in FIG. 11.
(7) NMR spectrum: Shown in FIG. 12.
(8) Color reactions (on thin silica gel layer):

| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

(9) Solubility:
　Insoluble in water. Soluble in methanol, acetone, ethyl acetate, chloroform and hexane.
(10) Distinction of basic, acidic or neutral: Neutral.

Figure 13:
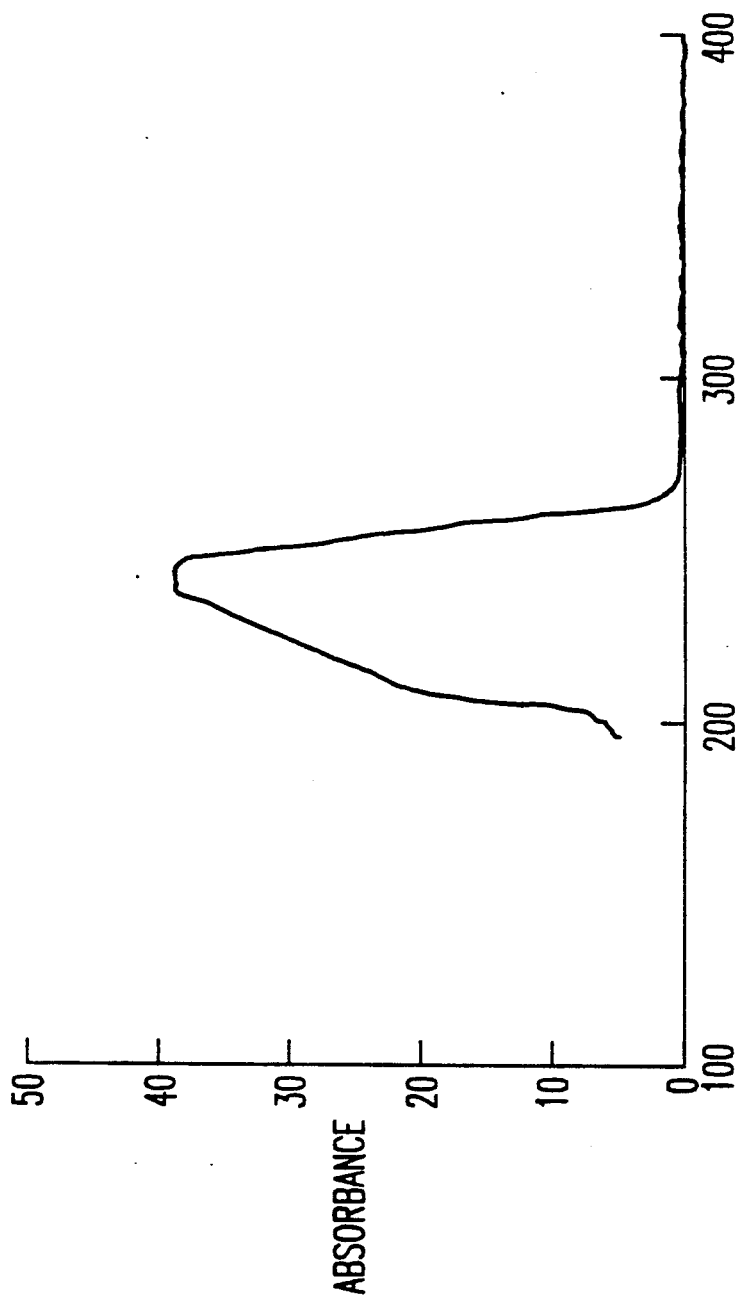
FIG. 13 shows an ultraviolet absorption spectrum of KSB-1939S$_5$, FIG. 14 an infrared absorption spectrum of KSB-1939S$_5$, and FIG. 15 an nuclear magnetic resonance spectrum of KSB-1939S$_5$.
Figure 14:
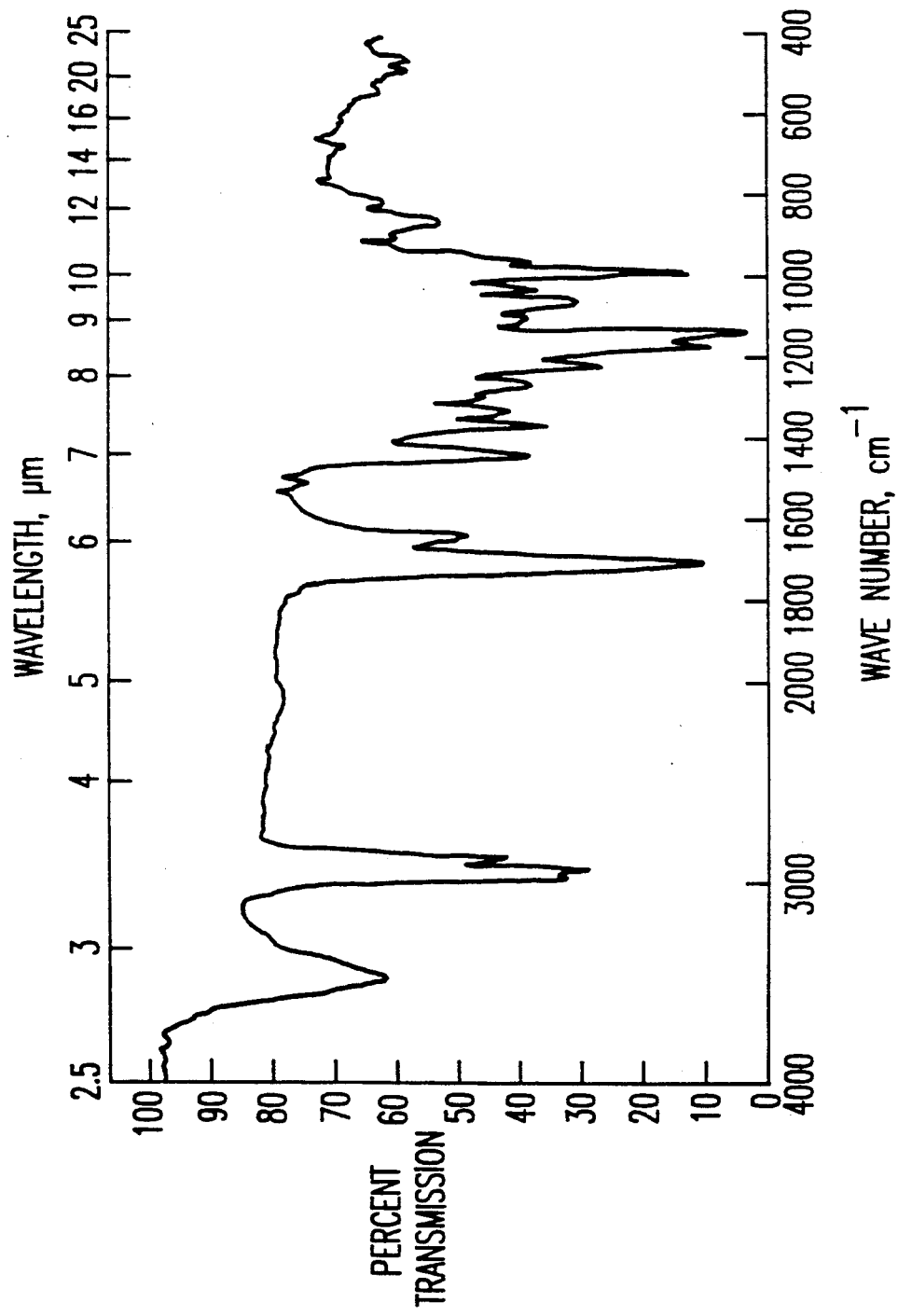
Figure 15:
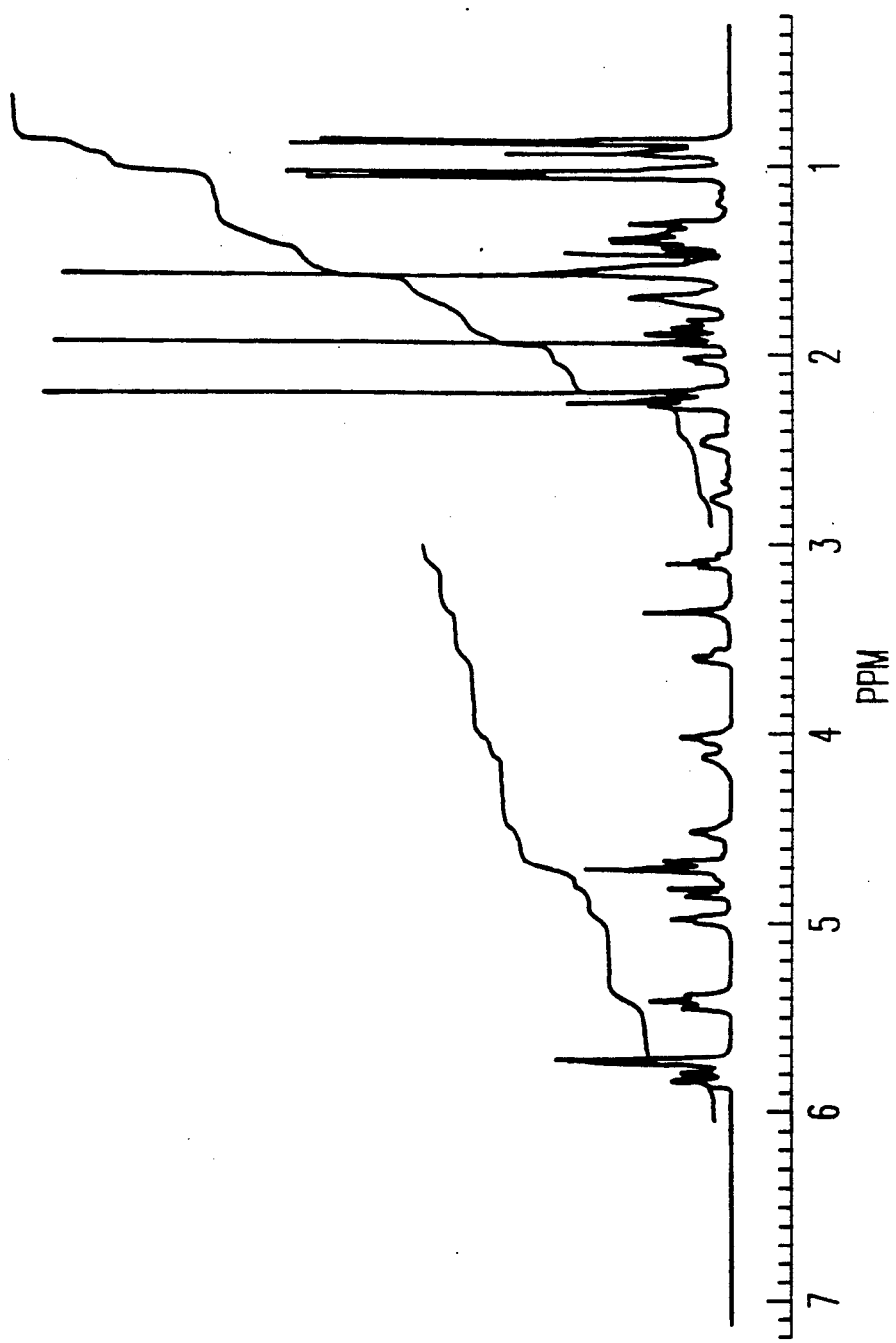

---
KSB-1939 S$_5$:

(1) Compound color: Colorless
(2) Elemental analysis data:
　C: 69.38%
　H: 8.13%
　O: 22.50%
(3) Molecular formula: C$_{37}$H$_{52}$O$_9$
(4) Molecular weight: 640 (FDMS)
(5) UV spectrum: Shown in FIG. 13.
(6) IR spectrum: Shown in FIG. 14.
(7) NMR spectrum: Shown in FIG. 15.
(8) Color reactions (on thin silica gel layer):

| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

-continued

(9) Solubility:
Insoluble in water. Soluble in methanol, acetone, ethyl acetate, chloroform and hexane.

(10) Distinction of basic, acidic or neutral: Neutral.

Figure 16:
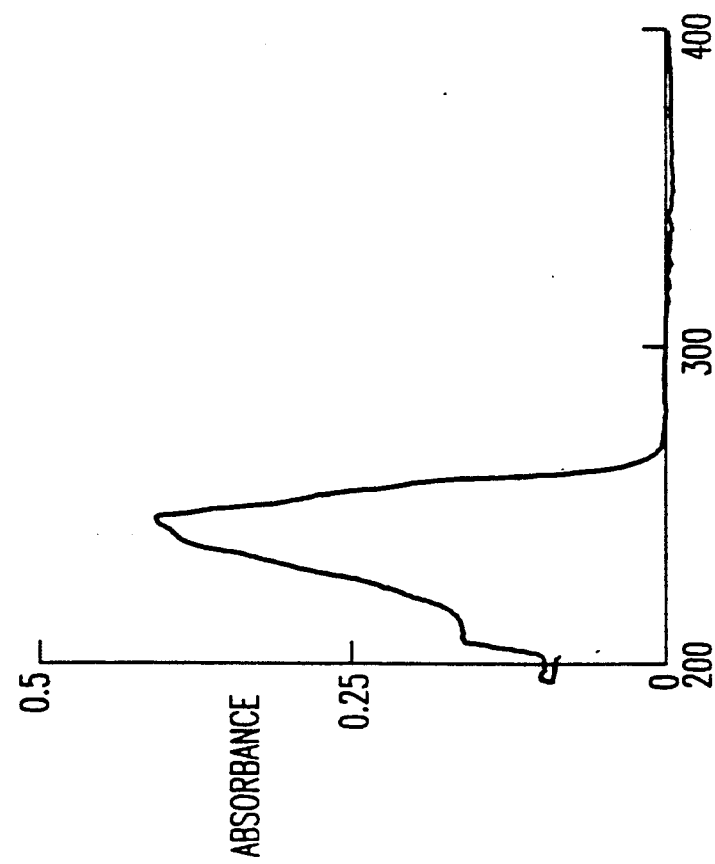
FIG. 16 shows an ultraviolet absorption spectrum of KSB-1939L$_{3\alpha}$, FIG. 17 an infrared absorption spectrum of KSB-1939L$_{3\alpha}$, and FIG. 18 an nuclear magnetic resonance spectrum of KSB-1939L$_{3\alpha}$.
Figure 17:
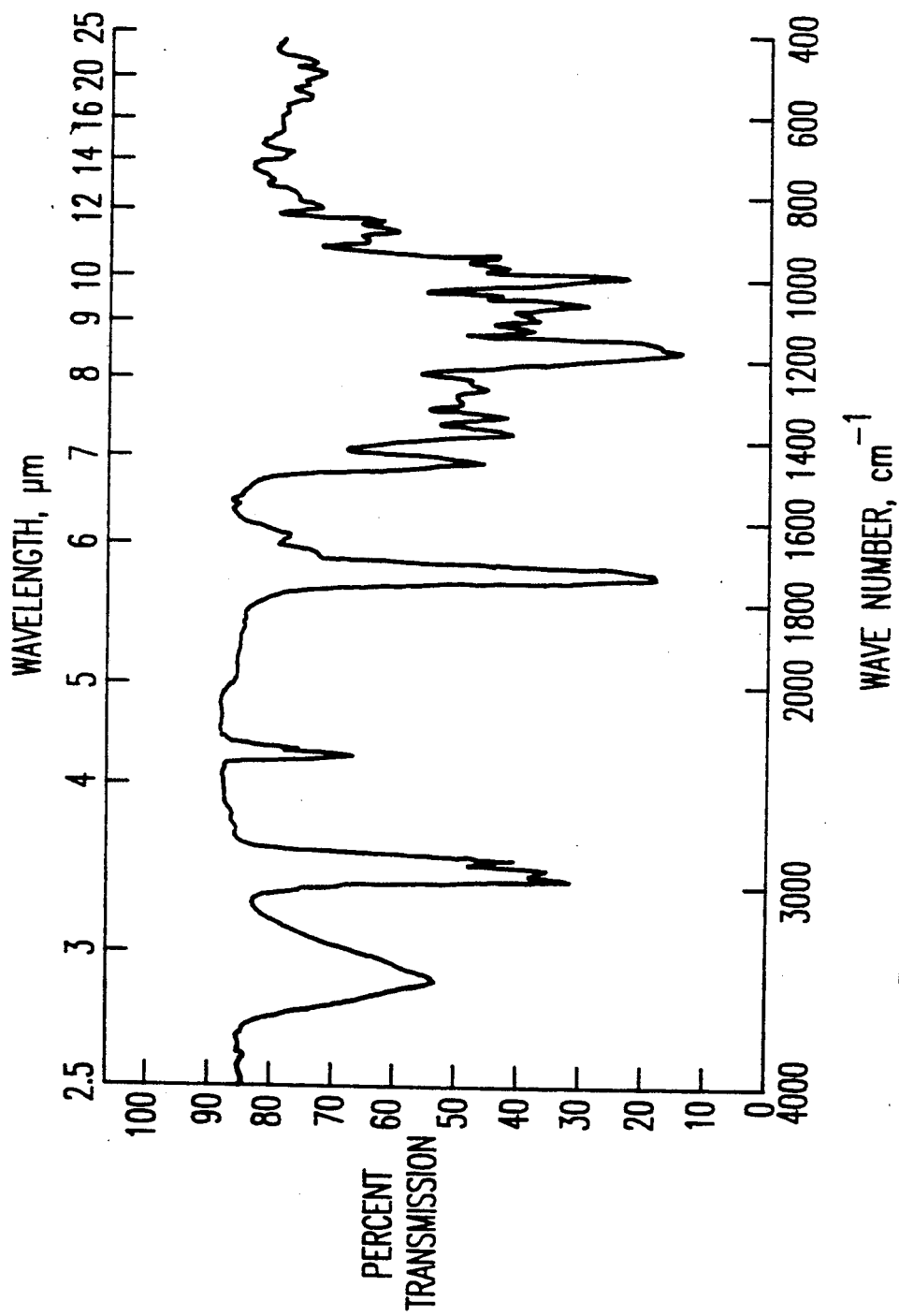
Figure 18:
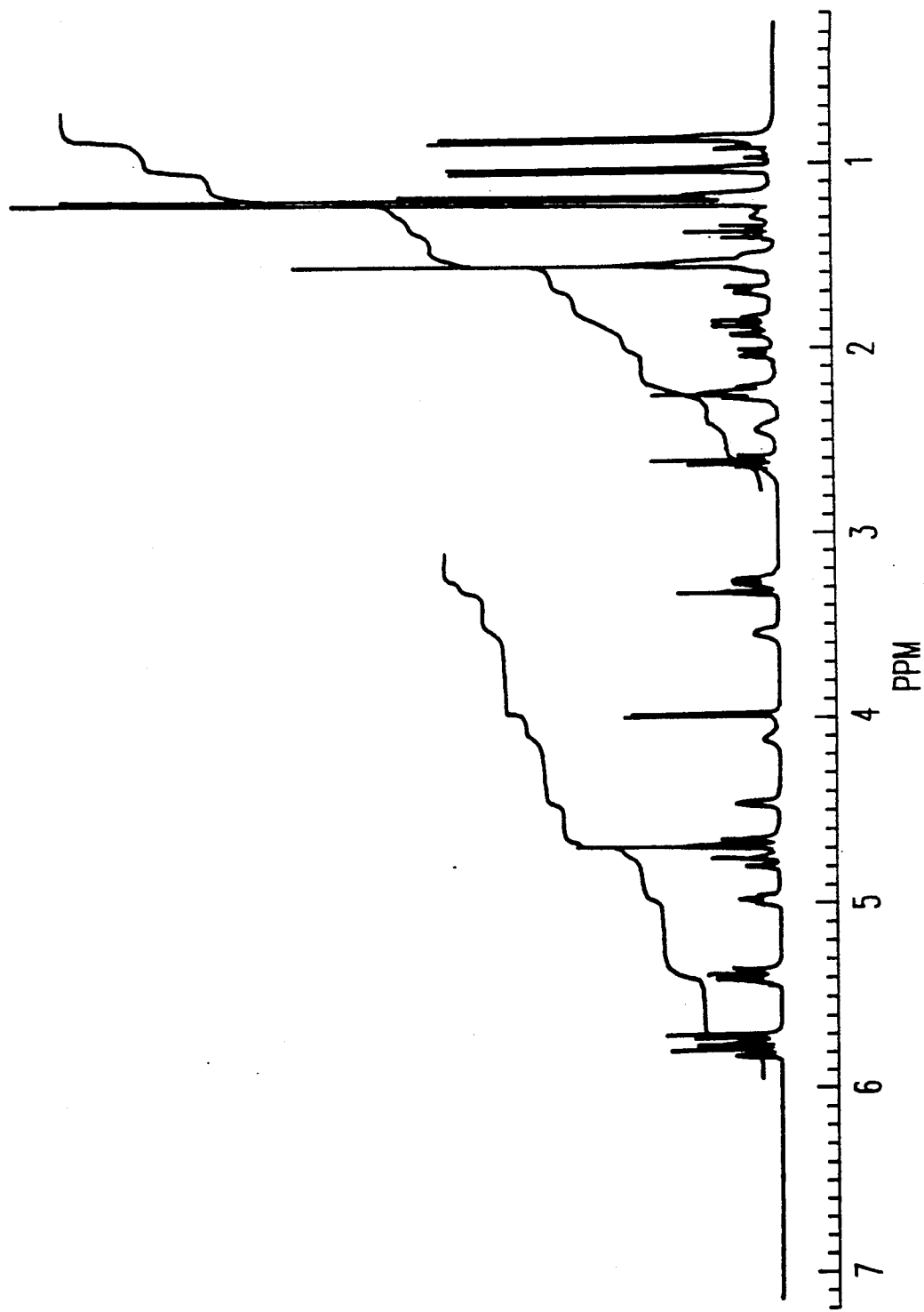

KSB-1939L$_{3\alpha}$:

(1) Compound color: Colorless
(2) Elemental analysis data:
  C: 68.40%
  H: 8.14%
  O: 23.45%
(3) Molecular formula: $C_{35}H_{50}O_9$
(4) Molecular weight: 614 (FDMS)
(5) UV spectrum: Shown in FIG. 16.
(6) IR spectrum: Shown in FIG. 17.
(7) NMR spectrum: Shown in FIG. 18.
(8) Color reactions (on thin silica gel layer):

| | |
|---|---|
| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction | + |

(9) Solubility:
Insoluble in water. Soluble in methanol, acetone, ethyl acetate, chloroform and hexane.
(10) Distinction of basic, acidic or neutral: Neutral.

Figure 19:
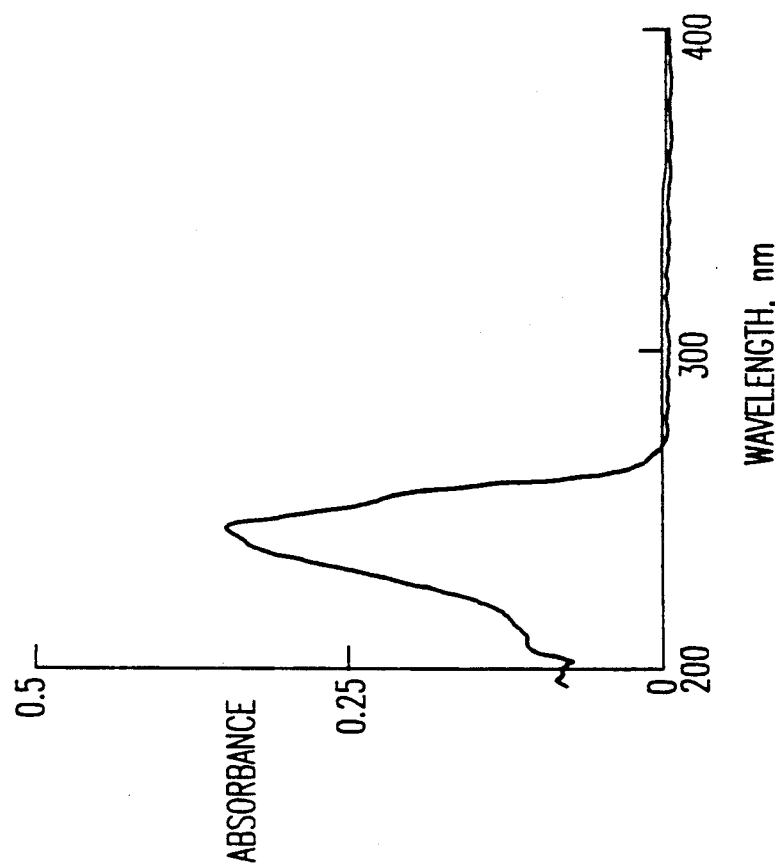
FIG. 19 shows an ultraviolet absorption spectrum of KSB-1939L$_{3\beta}$, FIG. 20 an infrared absorption spectrum of KSB-1939L$_{3\beta}$, and FIG. 21 an nuclear magnetic resonance spectrum of KSB-1939L$_{3\beta}$.
Figure 20:
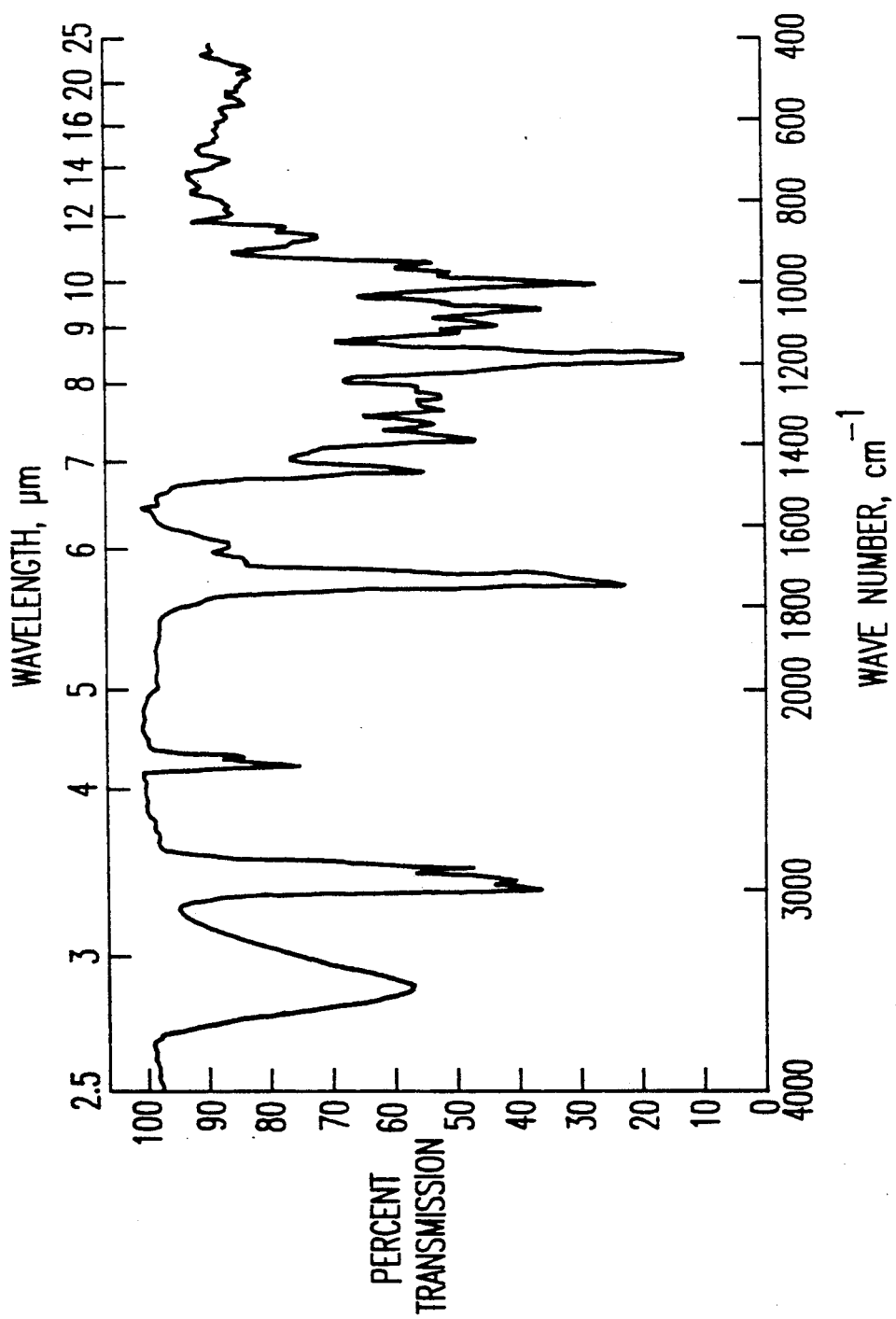
Figure 21:
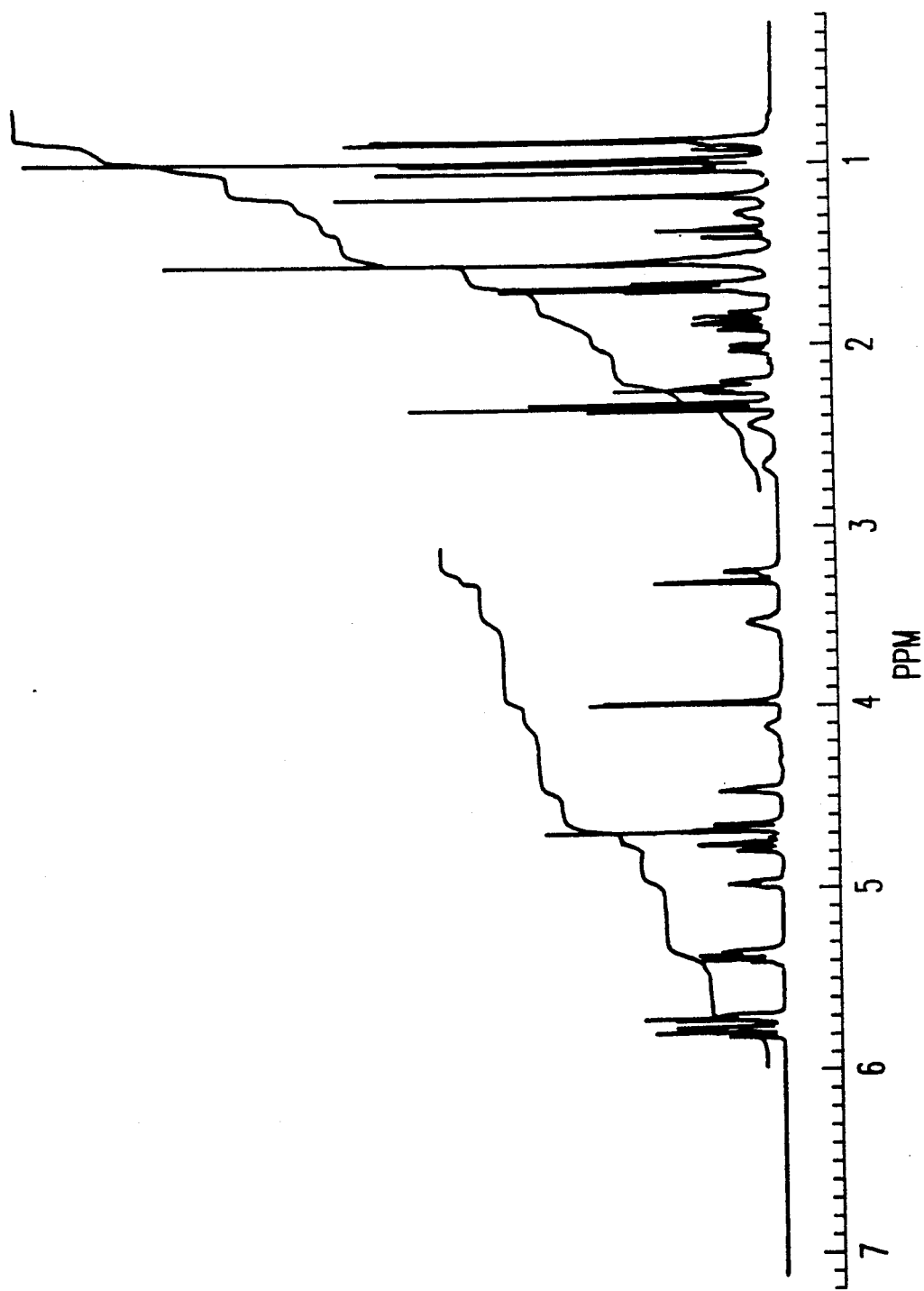

KSB-1939L$_{3\beta}$:

(1) Compound color: Colorless
(2) Elemental analysis data:
  C: 68.40%
  H: 8.14%
  O: 23.45%
(3) Molecular formula: $C_{35}H_{50}O_9$
(4) Molecular weight: 614 (FDMS)
(5) UV spectrum: Shown in FIG. 19.
(6) IR spectrum: Shown in FIG. 20.
(7) NMR spectrum: Shown in FIG. 21.
(8) Color reactions (on thin silica gel layer):

| | |
|---|---|
| Iodine reaction: | + |
| Sulfuric acid reaction: | + |
| Ninhydrin reaction: | − |
| Anisaldehyde reaction: | − |
| Ferric chloride reaction: | − |
| 2,4-Dinitrophenylhydrazine reaction: | + |

(9) Solubility:
Insoluble in water. Soluble in methanol, acetone, ethyl acetate, chloroform and hexane.
(10) Distinction of basic, acidic or neutral: Neutral.

From an analysis of the above physiochemical properties of the KSB-1939 compounds according to this invention, especially, their ultraviolet absorption spectra, infrared absorption spectra, and proton and carbon nuclear magnetic resonance spectra, the compounds were found to be 16-membered macrolide compounds. There are no known macrolide compounds corresponding to the molecular weights of the individual compounds determined from their mass analysis data (EI and FAB), so that their novelty has been verified.

As macrolide compounds which may be considered to be structurally analogous to the compounds of this invention, milbemycins and avermectins may be mentioned. Of these, 20 kinds of milbemycins have heretofore been reported in total, dated back to The Journal of Antibiotics, 29, 76 (1976); and 31 kinds of avermectins dated back to Antimicrobial Agents and Chemotherapy, 15, 361 (1979). In addition, 4 analogous compounds led by LL-F28249α are reported on page 402 of Journal of Chemical Society Chemical Communication (1987).

They are all substances produced by actinomycetes of Steptomyces and called "insecticidal macrolides". As to analyses of their structures, reference may be had to Abstract Papers, 309–316, 18th Symp. Chem. Natural Products, Kyoto, October 17–19, 1974 and Tetrahydron Letters, 711–714 (1975) in regard to milbemycins; to Journal of American Chemical Society, 103, 4216–4221 (1981) in connection to avermectins; and to the above-described article with regard to LL-F28249.

Various data of the KSB-1939 compounds of this invention were compared with the structural analysis data disclosed in these articles. As a result, the KSB-1939 compounds of this invention have been found to have such characteristic features that:

(1) they are compounds having the general formula (I) and containing, as a fundamental skeleton, the lactone ring described in Journal Antibiotics, 33, 1121 (1980);

(2) no saccharide side chain such as that seen in avermectins is present at the 13-position of the macrolide ring; and (3) there is a methyl group at the 24-position of the spira ring.

The following characteristic features may also be mentioned by way of example.

(4) KSB-1939H$_2$-H$_5$ as well as KSB-1939L$_{3\alpha}$ and L$_{3\beta}$ have a methyl group at the 25-position, while KSB-1939S$_5$ contains an ethyl group at the 25-position.

(5) A characteristic feature of KSB-1939H$_2$ resides in the side chain bonded to the 4-carbon and a 3-methyl-2-butenoyloxymethyl group is bonded to the 4-carbon of the macrolide ring.

(6) A characteristic feature of KSB-1939H$_3$ resides in the side chain bonded to the 4-carbon and a 3-methyl-2-butanoyloxymethyl group is bonded to the 4-carbon of the macrolide ring.

(7) KSB-1939H$_4$ contains a 3-methyl-2-pentenoyloxymethyl group bonded to the 4-carbon of the macrolide ring.

(8) KSB-1939H$_5$ contains a 4-methyl-2-pentanoyloxymethyl group bonded to the 4-carbon of the macrolide ring.

(9) A characteristic feature of KSB-1939S$_5$ resides in the side chain bonded to the 4-carbon and a 3-methyl-2-butenoyloxymethyl group is bonded to the 4-carbon of the macrolide ring.

(10) A characteristic feature of KSB-1939L$_{3\alpha}$ resides in the side chain bonded to the 4-carbon and a 2-methylpropanolyloxymethyl group is bonded to the 4-carbon of the macrolide ring.

(11) A characteristic feature of KSB-1939L$_{3\beta}$ resides in the side chain bonded to the 4-carbon and a butanoyloxymethyl group is bonded to the 4-carbon of the macrolide ring. From the foregoing, the present inventors have determined KSB-1939 compounds as novel compounds represented by the general formula (I).

The compounds of this invention obtained as described above have insecticidal and acaricidal effects and anthelmintic activities against animal parasites.

As insects and other pests against which KSB-1939 compounds of this invention are effective, the following insects and other pests may be mentioned by way of example.

Hemiptera

Green rice leafhopper (*Nephotettix cincticeps* Uhler), brown rice planthopper (*Nilaparvata lugens* Stal), small brown planthopper (*Laodelphax striatellus* Fallen), whitebacked rice planthopper (*Sogatella furcifera* Horuath), green peach aphid (*Myzus persicae* Sulzer), cotton aphid (*Aphis gossypii* Glover), turnip aphid (*Lipahis erysimi* Kaltenbach), and greenhouse whitefly (*Trialeurodes vaporariorum* Westwood).

- Lepidoptera

Diamondback moth (*Plutella xylostella* Linne), common cabbageworm (*Pieris rapae crucivora* Boisduval), common cutworm (*Spodoptera Litura* Fabricius), and Asiatic rice borer (*Chilo suppressalis* Walker).

Coleoptera

Rice water weevill (*Lissorhoptrus oryzophilus* Kuschel), adzuki bean weevil (*Callosobruchus chinensis* Linne), twenty-eight-spotted ladybird (*Henosepilachna vigintioctopunctata* Fabricius), and Japanese beetle (*Popillia japonica* Newman)

Diptera

Housefly (*Musca domestica* Linne), house mosquito (*Culex pipiens pallens* Coguillett), and seedcorn maggot (*Hylemya platura* Meigen).

Orthoptera

German cockroach (*Blattella germanica* Linne), and American cockroach (*Periplaneta americana* Linne).

Mites

Twospotted spider mite (*Teranychus urticae* Koch), carmine spider mite (*Tetranychus cinnabarinus* Boisduval), Kanzawa spider mite (*Tetranychus kanzawai* Kishida), citrus red mite (*Panonychus citri* McGregor), and European red mite (*Panonychus ulmi* Koch).

Nematodes

Southern root-knot nematode (*Meloidoqyne incognita* Kofoid et White), Cobb root-lesion nematode (*Pratylenchus penetrans* Cobb), and soybean cyst nematode (*Heterodera glycines* Ichinohe).

Among these, KSB-1939 compounds of this invention are extremely effective, in particular, against Hemiptera such as brown rice planthopper and green rice leafhopper, twospotted spider mite, and Kanzawa spider mite.

When the compounds of this invention are used as insecticidal and acaricidal agents, they may be used as they are. However, it is generally more preferable to use each of them as a preparation by mixing it with a carrier, surfactant, dispersant, adjuvant or the like and then formulating the resultant mixture into a preparation such as dust, wettable powder, emulsion or granules by way of example in a manner known per se in the art. As suitable carriers, may be mentioned solid carriers such as clay, talc, bentonite, diatomaceous earth, white carbon, kaolin, vermiculite, hydrated lime, siliceous sand, ammonium sulfate and urea as well as liquid carriers such as xylene, toluene, methyl ethyl ketone, isopropyl alcohol, (di)methylnaphthalene and cyclohexanone. Exemplary surfactants and dispersants may include metal alkyl benzene sulfonates, polyoxyethylene alkyl aryl ether, sodium alkylsulfonates, sodium alkylnaphthalenesulfonates, sodium dinaphthylmethanesulfonate, and sodium ligninsulfonate. As exemplary adjuvants, may be mentioned carboxymethylcellulose, polyethylene glycol, gum arabic, etc. These preparations may be sprayed or dusted after diluting them to a suitable concentration, or may be applied directly.

The application rate of each compound of the present invention varies depending on the type of the compound contained, the insect or pest to be treated, the nature of outbreak, the degree of damages, environmental conditions, the preparation form employed, etc. When employed eventually in a liquid form such as an emulsion or wettable powder, it is suitable to choose the application rate from a range of 0.001–1,000 ppm, preferably, 0.1–100 ppm. When used as is like dust or granules, the application rate may be suitably chosen from a range of 1–1,000 g, preferably, 5–100 g per 10 ares.

Since each compound of this invention has anthelmintic activities against nematodes, especially, antiendoparasitic activities and/or anti-ectoparasitic activities, it can be used for the treatment of animals and/or men infected by endoparasitic organisms and/or ectoparasitic organisms.

Endoparasitic organisms and ectoparasitic organisms infect men and various animals and in particular, are found widely in livestock such as pigs, cows, sheep, goats and poultry (domestic fowls and turkeys); horses; rabbits; birds to be hunted; caged birds; and house animals such as dogs, cats, Guinea pigs, gerbils and hamsters. Infection of livestock to parasites, their anemic malnutrition and their weight loss are a major cause for the economical loss in the world.

Illustrative genus examples of such endoparasitic organisms that infect animals and/or men may include Ancylostoma, Ascaridia, Ascaris, Aspicularis, Brugia, Bunostomum, Capillaria, Charbertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Stonoyloides, Syphacia, Toxascaris, Toxocara, Trichonema, Trichostrongylus, Trichinella, Trichuris, Triodontophrous, Uncinaria and Wuchereria.

As illustrative examples of ectoparasitic organisms which infect animals and/or men, there are ectoparasitic Arthropods such as biting insects, fleas, ticks, sucking insects and other Diptera insects.

Illustrative genus examples of such ectoparasitic organisms which infect animals and/or men may include Ambyloma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Luchilia, Melophagus, Oestrus, Otobius, Otodectes, Psorerqates, Psoroptes, Rhipicephalus, Sarcoptes, Stomoxys and Tabanus.

Each compound of this invention has been found to be effective against a wide range of endoparasitic organisms and ectoparasitic organisms in vitro and in vivo. Antibiotic properties of each compound of this invention can be demonstrated, for example, by its activities against microfilariae of *Dirofilaria immitis*. In particular, each compound of this invention has been found to be active against nematodes such as *Toxocara canis* in vivo.

The minimum effective dose (minimum lethal dose) of each compound of this invention for killing microfilariae of *Dirofilaria immites* was determined by in vitro procedures. The substance of this invention has been found to be effective against the nematoda even at an application rate lower than 5 µg/ml. The compounds of this invention are generally free of toxicity at a physiologically-effective level.

When each compound of this invention is used as an anthelmintic, it is only necessary to administer it in the form of a suitable preparation which conforms with a host animal to be treated and the kind of a parasite to be expelled. For example, it may be administered orally in the form of capsules, pills, tablets or an aqueous solution or by injection. Such preparations can be formulated in a usual manner, following a standard veterinary and/or medical procedure. Namely, capsules, pills or tablets can be produced by mixing the active ingredient with a suitable particulate diluent or carrier which additionally contains a disintegrant and/or binder such as starch, lactose, talc or magnesium stearate. An aqueous solution can be produced by dispersing the active ingredient in an aqueous solution which contains a dispersant or wetting agent. On the other hand, an injection can be produced in the form of an aseptic solution which may contain another substance, for example, buffer salts or glucose in an amount sufficient to render the solution isotonic with blood. The weights of the active ingredient in these preparations vary depending on the species of a host animal to be treated, the seriousness and type of infection and the weight of the host animal. For oral administration, a dose of about 0.01-10 mg per kg of an animal may be sufficient when administered at once or in portions over a period of from 1 day to 5 days. Needless to say, another dose range either higher or lower than the above range may also be indicated in some instances.

As an alternative, each compound of this invention may be administered along with animal feed. A concentrated feed supplement or premix may be produced in order to mix it with an ordinary animal feed.

EXAMPLES

This invention will next be described more specifically by the following Examples. It should however be borne in mind that the present invention is not limited to the following Examples.

EXAMPLE 1

A piece of a subcultivation slant of KSB-1939 strain was transferred to each of 500-ml Erlenmeyer flasks filled with 100 ml of a seed culture medium which contained 1.0% of malt extract, 0.4% of yeast extract, 0.4% of glucose and 0.2% of defatted soybean meal. Seed cultivation was conducted at 28° C. for 3 days on a shaker. Placed in a jar fermenter was 20 l of a production medium containing 3% of glucose, 0.5% of defatted soybean meal, 0.2% of yeast extract, 0.2% of dipotassium phosphate, 0.05% of magnesium sulfate and 0.05% of "Pronal 502" (trade name; product of Toho Chemical Industry Co., Ltd.). After sterilizing and cooling the production medium, 5 flasks of the above seed culture were inoculated to the production medium. Cultivation was conducted for 9 days at an aeration rate of 20 l/min, a cultivation temperature of 30° C. and a stirring speed of 200 r.p.m. After completion of the cultivation, the resultant culture was subjected to suction filtration by using celite as an aid, whereby wet cells were collected. The wet cells were dispersed in 10 l of methanol, and the resultant dispersion was stirred for 1 hour to achieve extraction. A clear methanol solution was then recovered by filtration. The extract was concentrated to a final volume of 100 ml under reduced pressure, followed by an addition of 100 ml of methanol. The resultant mixture was extracted twice with 500 ml of hexane. The hexane solution was concentrated under reduced pressure, thereby recovering about 7 g of a crude product. The crude product was dissolved in a small amount of a solvent which had been obtained by adding 15 parts of acetone to 85 parts of hexane. The thus-prepared solution was developed by chromatography on a silica gel column having an inner diameter of 50 mm and a height of 650 mm by the same solvent. Active fractions were collected and then concentrated to dryness under reduced pressure, thereby obtaining 1.1 g of a crude powder mixture which contained 25% of KSB-1939H$_2$, 6% of KSB-1939H$_3$, 8% of KSB-1939H$_4$, 3% of KSB-1939H$_5$, 12% of KSB-1939S$_5$ and 3% of a KSB-1939L$_{3\alpha}$-KSB-1939L$_{3\beta}$ mixture.

EXAMPLE 2

Dissolved in 5 ml of acetonitrile was 250 mg of the crude powder mixture obtained in Example 1. One milliliter of the resultant solution was injected into a fractionating high-performance liquid chromatograph equipped with an ODS column whose inner diameter and length were 20 mm and 250 mm respectively. By feeding 80% acetonitrile at a flow rate of 10 ml/min, individual components were fractionated by ultraviolet absorption at 240 nm. Chromatographic fractions of 5 operations were combined and concentrated to dryness, so that the following components were obtained in a purified form.

|  | Purity | Yield |
| --- | --- | --- |
| KSB-1939H$_2$ | 96% | 57 mg |
| H$_3$ | 98 | 11 |
| H$_4$ | 97 | 14 |
| H$_5$ | 97 | 4 |
| S$_5$ | 65 | 35 |
| L$_{3\alpha\beta}$ mixture | 80 | 6 |

Purified products of from H$_2$ to H$_5$ were dissolved in a small amount of methanol, followed by an addition of several droplets of water. A precipitate thus formed was recovered and dried, thereby separately obtaining 45 mg of H$_2$, 7 mg of H$_3$, 10 mg of H$_4$ and 3 mg of H$_5$ as purified products. In addition, S$_5$ and L$_{3\alpha\beta}$ mixture were subjected to high-performance liquid chromatography on a silica gel column having an inner diameter of 8 mm and a length of 250 mm and were then developed by 4 ml/min of a 98:2 mixture of hexane and acetone. Relevant fractions were collected and concentrated to dryness, thereby separately obtaining 17 mg of S$_5$, 2 mg of L$_{3\alpha}$ and 2 mg of L$_{3\beta}$ as purified products.

EXAMPLE 3

A piece of a subcultivation slant of KSB-1939 strain was transferred to each of 500-ml Erlenmeyer flasks filled with 100 ml of a seek culture medium which contained 1.0% of malt extract, 0.4% of yeast extract, 0.4% of glucose and 0.2% of defatted soybean flour. Seed cultivation was conducted at 28° C. for 3 days on a shaker. Placed in a jar fermenter was 20 l of a production medium containing 3% of starch, 0.5% of yeast extract, 0.5% of corn steep liquor, 0.2% of dipotassium phosphate, 0.05% of magnesium sulfate and 0.05% of "Pronal 502" (trade name; product of Toho Chemical Industry Co., Ltd.). After sterilizing and cooling the production medium, the above seek culture were inoculated to the production medium. Cultivation was conducted for 9 days at an aeration rate of 20 l/min, a cultivation temperature of 28° C. and a revolutionary speed of 150 revolutions/min. After completion of the cultivation, the resultant culture was subjected to suction filtration by using celite as an aid, whereby wet cells were collected. The wet cells were disperse in 10 l of acetone, and the resultant dispersion as stirred for 1 hour to achieve extraction. A clear acetone solution was then recovered by filtration. The extract was concentrated under reduced pressure so as to distill off the acetone. The residue was washed with 200 ml of water and was then extracted twice with 500 ml of ethyl acetate. Fifty grams of anhydrous sodium sulfate were added to about 1 l of the thus-prepared ethyl acetate solution to eliminate water. The resultant solution was concentrated under reduced pressure to distill off the ethyl acetate, so that about 6 g of an oily matter was recovered. The oily matter was dissolved in a small amount of a developer which had been obtained by adding 5 parts of acetone to 95 parts of chloroform. The thus-prepared solution was subjected to chromatography on a silica gel column having an inner diameter of 50 mm and a height of 650 mm. An eluate was collected in 20-ml fractions. Active fractions were collected and concentrated to dryness under reduced pressure to obtain 650 mg of a roughly-purified mixture containing KSB-1939$H_2$, $H_3$, $H_4$ and $H_5$ and 90 mg of a roughly-purified mixture containing KSB-1939$S_5$ separately.

EXAMPLE 4

Dissolved in 5 ml of acetonitrile was 200 mg of the roughly-purified powder mixture containing KSB-1939$H_2$-$H_5$ and obtained in Example 3. One milliliter of the resultant solution was injected into a fractionating high-performance liquid chromatograph equipped with an ODS column whose inner diameter and length were 20 mm and 250 mm respectively. By feeding 80% acetonitrile as an eluent at a flow rate of 10 ml/min, various active fractions were collected by detecting their components by ultraviolet absorption at 240 nm. The fractions were separately concentrated to dryness, so that the following components were obtained.

|  | Purity | Yield |
|---|---|---|
| KSB-1939$H_2$ | 96% | 18 mg |
| $H_3$ | 98 | 10 |
| $H_4$ | 97 | 11 |
| $H_5$ | 97 | 15 |

Purified products of from $H_2$ to $H_5$ were dissolved in a small amount of methanol, followed by an addition of several drops of water. A precipitate thus formed was recovered and dried, thereby separately obtaining 10 mg of $H_2$, 5 mg of $H_3$, 6 mg of $H_4$ and 9 mg of $H_5$ as purified products.

EXAMPLE 5

Dissolved in 2 ml of acetonitrile was 50 mg of the roughly-purified product obtained in Example 3 and containing KSB-1939$S_5$. The resulting solution was then subjected to high-performance liquid chromatography under the same conditions as in Example 4, thereby obtaining 15 mg of KSB-1939$S_5$ whose purity was 65%. It was dissolved in 1 ml of hexane, injected into a fractionating liquid chromatography equipped with a silica gel column having an inner diameter of 20 mm and a length of 250 mm, and developed by a 98:2 mixture of hexane and isopropyl alcohol. SKB-1939$S_5$ fractions were collected and then dried under reduced pressure, so that 8.5 mg of KSB-1939$S_5$ was obtained as a purified product.

The present invention will be described further with reference to Preparation Examples. Needless to say, the present invention is not necessarily limited to the following exemplary compositions but may adopt compositions varied in a wide range. In the following Preparation Examples, all designations of "part(s)" means part(s) by weight.

Preparation Example 1 (Dust)

A dust was formulated by intimately grinding and mixing 0.5 part of KSB-1939$H_2$, 5 parts of diatomaceous earth and 94.5 parts of clay.

Preparation Example 2 (Wettable Powder)

A wettable powder was formulated by intimately grinding and mixing 2 parts of KSB-1939$H_3$, 53 parts of diatomaceous earth, 40 parts of clay, 2 parts of sodium dinaphthylmethanedisulfonate and 3 parts of sodium ligninsulfonate.

Preparation Example 3 (Emulsion)

An emulsion was formulated by uniformly dissolving 2 parts of KSB-1939$S_5$, 85 parts of isobutyl oleate and 13 parts of "New Calgen D-405" (trade name; product of Takemoto Oil & Fat Co., Ltd.).

Preparation Example 4 (Emulsion)

An emulsion as formulated by uniformly dissolving 2 parts of KSB-1939$H_5$, 60 parts of machine oil, 20 parts of cyclohexanone and 18 parts of "Sorpol KT" (trade name; product of Toho Chemical Industry Co., Ltd.).

Preparation Example 5 (Granules)

KSB-1939$H_4$ (0.5 part), 2 parts of the sodium salt of lauryl sulfate, 5 parts of sodium lignin-sulfonate, 2 parts of carboxymethylcellulose and 90.5 parts of clay were intimately ground and mixed. The resultant mixture was added and kneaded with 20 parts of water. After forming the resultant mass into granules of 14–32 mesh by means of an extrusion granulator, they were dried into granules.

Preparation Example 6 (Tablets)

| KSB-1939$L_{3\alpha}$ | 50.0 mg |
|---|---|
| Calcium stearate | 5.0 mg |

Microcrystalline cellulose is added to make the weight of each tablla core be 75.0 mg.

KSB-1939$L_{3\alpha}$, calcium stearate and microcrystalline cellulose are blended. The blend is compacted into slugs. The slugs are passed through a rotary granulator, whereby they are broken into free-flowing granules. The granules are pressed into tablets. If necessary, the tablets may be film-coated as core tablets with hydroxypropylmethylcellulose or a like film-forming material by using either an aqueous or a non-aqueous solvent system. A plasticizer and/or a suitable colorant may be incorporated in the film-coating liquid formulation.

Preparation Example 7 (Tablets)

| KSB-1939$H_2$ | 250.0 mg |
|---|---|
| Calcium stearate | 5.0 |
| Corn starch | 25.0 |
| Sodium starch glycolate | 10.0 |
| Sodium lauryl sulfate | 5.0 |

Microcrystalline cellulose is added to make the weight of each tablla core be 450 mg.

KSB-1939$H_2$ is added with a sufficient amount of a 10% starch paste to prepare a wet mixture suitable for granulation. The wet mixture is formed into granules while drying same in a tray or fluidized bed drier. The resultant granules are sifted. The thus-classified granules are added with the remaining components and then pressed into tablets.

If necessary, the tablets may be film-coated as tablet cores.

Preparation Example 8 (Oral Drench)

| KSB-1939L$_{3\beta}$ | 0.5 w/v % |
|---|---|
| Polysolvate 85 | 5.0 |
| Benzyl alcohol | 3.0 |
| Polyvinylpyrrolidone K25 | 30.0 |

Phosphate buffer may be added to adjust the pH to 6.0–6.5. Water is added to a total volume of 100.0.

KSB-1939L$_{3\beta}$ is added with Polysolvate 85, benzyl alcohol and Polyvinylpyrrolidone K25 to dissolve same. A portion of the water is added and if necessary, the pH of the resultant solution is adjusted to 6.0–6.5. The remaining portion of the water is added to the final volume. Drench bottles are filled with the resultant formulation.

The preferable proportion of an active ingredient may range from 0.01 to 5 w/v % when an oral drench is prepared.

Preparation Example 9 (Oral Paste)

| KSB-1939H$_2$ | 10.0 w/v % |
|---|---|
| Saccharin sodium | 25.0 |
| Polysolvate 85 | 3.0 |
| Aluminum distearate | 5.0 |

Fractionated coconut oil is added to a total volume of 100.0.

Aluminum distearate is dispersed under heating in the fractionated coconut oil and Polysolvate 80. The resultant dispersion is cooled to room temperature and saccharin sodium is dispersed in the resultant oily vehicle. KSB-1939H$_2$ is mixed with the thus-prepared dispersion. The resultant mixture is then filled in a plastic syringe.

The preferable proportion of an active ingredient may range from 1 to 30 w/v % when an oral paste is prepared.

Preparation Example 10 (Parenteral Injection)

| KSB-1939H$_3$ | 5.0 w/v % |
|---|---|
| Benzyl alcohol | 2.0 |
| Glyceryl triacetate | 30.0 |

Polyethylene glycol 300 is added to a total volume of 100.0.

KSB-1939H$_3$ is dissolved in benzyl alcohol and glyceryl triacetate, followed by an addition of polyethylene glycol 300 to the prescribed volume. The resultant formulation is packed sterilely by a routine pharmaceutical method, for example, by bacterial filtration or by pasturization in an autoclave.

The preferable proportion of an active ingredient may range from 0.1 to 10 w/v % when a parenteral injection is prepared.

Preparation Example 11 (Aerosol Spray)

| KSB-1939H$_4$ | 0.1 w/v % |
|---|---|
| Trichloroethane | 29.9 |
| Trichlorofluormethane | 35.0 |
| Dichlorodifluoromethane | 35.0 |

KSB-1939H$_4$ is mixed with trichloroethane. The resultant mixture is filled in an aerosol bottle. The top space is purged with a gaseous propellant and a valve is adjusted at an appropriate position. The liquid propellants are then filled as needed under pressure through the valve. An actuator and a dust cap are applied.

The preferable proportion of an active ingredient may range from 0.01 to 5 w/v % when an aerosol spray is prepared.

Effects which the compounds of the present invention can exhibit will hereinafter be described by the following Tests.

Test 1 (Miticidal Test against Adult Female Twospotted Spider Mite)

Each of polyethylene-made cups having a diameter of 55 mm and filled with water was covered with a lid through which a hole having a diameter of 10 mm was formed centrally. Absorbent cotton was suspended through the hole of the lid so as to absorb water. A sheet of filter paper was placed on the lid. Two bean leaf disks were place don the filter paper so that the disks were always supplied with water. Using a writing brush, adult female two spotted spider mites were inoculated at a rate of 10 mites per leaf disk. Twenty-four hours later, abnormal mites were removed, and wettable powders which had been prepared in accordance with the procedures of Preparation Examples 4–6 respectively were separately diluted to a predetermined concentration and sprayed to apply 2 mg/cm$^2$ of the respective agrochemical solutions. The test was conducted dually. Two days after the treatment with the agrochmical solutions, it was determined through a stereoscopic microscope whether the mites were alive or dead. The corrected mite mortality was calculated in accordance with the following equation. Results are summarized in Table 3.

Corrected mite mortality (%) =

$$\left( \frac{\text{Mite mortality of treated group} - \text{Mite mortality of untreated group}}{100 - \text{Mite mortality of untreated group}} \right) \times 100$$

TABLE 3

| Tested agrochemical | Concentration of agrochemical (ppm) | Corrected mite mortality (%) |
|---|---|---|
| KSB-1939H$_2$ | 1 | 100 |
| | 0.2 | 100 |
| | 0.004 | 70.1 |
| KSB-1939H$_3$ | 5 | 100 |
| | 1 | 100 |
| | 0.2 | 100 |
| KSB-1939H$_4$ | 1 | 100 |
| | 0.2 | 100 |
| | 0.04 | 94.2 |
| KSB-1939H$_5$ | 5 | 100 |
| | 1 | 100 |
| KSB-1939S$_5$ | 1 | 100 |
| | 0.2 | 100 |
| | 0.04 | 45.7 |
| Milbemycin (A3 30%, A4 70%) | 1 | 69.1 |
| | 0.2 | 15.0 |

Test 2

Following the procedure of Test 1, tests were conducted with respect to Kanzawa spider mite and twospotted spider mite so that their LC$_{50}$ values were determined. Results are shown in Table 4. Milbemycin was used as a control.

TABLE 4

| Tested Agrochemical | LC$_{50}$ (ppm) | |
|---|---|---|
| | Kanzawa spider mite | Twospotted spider mite |
| KSB-1939H$_2$ | 0.0465 | 0.0249 |
| KSB-1939S$_5$ | 0.0643 | 0.0339 |
| Milbemycin (A3 30%, A4 70%) | 0.485 | 0.339 |

Test 3 (Insecticidal Test against Brown Rice Planthopper)

Wettable powders which had been prepared following the procedures of Preparation Examples 4–6 respectively were diluted with water to a predetermined concentration. Rice stems and leaves were dipped in the resultant solutions and then dried in the air. They were placed in test tubes. Ten brown rice planthopper larvae were placed in each test tube. The test tubes were plugged with absorbent cotton and the larvae were reared for 5 days in a constant-temperature chamber of 25° C. The test was conducted dually. The numbers of larvae were counted after the rearing, whereby mortality values of brown rice planthopper were calculated. Results are summarized in Table 5.

TABLE 5

| Tested agrochemical | Concentration of agrochemical (ppm) | Planthopper mortality (%) |
|---|---|---|
| KSB-1939H$_2$ | 5 | 100 |
| | 1 | 95 |
| KSB-1939H$_3$ | 25 | 100 |
| | 5 | 65 |
| KSB-1939H$_4$ | 5 | 100 |
| | 1 | 65 |
| KSB-1939H$_5$ | 25 | 95 |
| KSB-1939S$_5$ | 5 | 100 |
| | 1 | 85 |

Test 4 (Insecticidal Test against Diamondback Moth)

Wettable powders which had been prepared following the procedures of Preparation Examples 4–6 respectively were diluted with water to a predetermined concentration. Cabbage leaves were dipped in the resultant solutions and then dried in the air. They were placed in polyethylene-made cups having a diameter of 55 mm. Ten 3rd-instar larvae of diamondback moth were placed in each cup. The larvae were reared for 5 days in a constant-temperature chamber of 25° C. The test was conducted dually. The numbers of dead larvae were counted after the rearing, whereby mortality values of diamondback moth were calculated. Results are summarized in Table 6.

TABLE 6

| Tested agrochemical | Concentration of agrochemical (ppm) | Moth mortality (%) |
|---|---|---|
| KSB-1939H$_3$ | 25 | 100 |
| KSB-1939H$_5$ | 25 | 100 |

Test 5 (Insecticidal Test against Asiatic Rice Borer)

Wettable powders which had been prepared following the procedures of Preparation Examples 4–6 respectively were diluted with water to a predetermined concentration. Sprouted unhulled rice seeds were dipped in the resultant solutions and then dried in the air. They were placed separately in polyethylene-made cups having a diameter of 55 mm. Ten 3rd-instar larvae of asiatic rice borer were placed in each cup. The larvae were reared for 5 days in a constant-temperature chamber of 25° C. The test was conducted dually. The numbers of dead larvae were counted after the rearing, whereby mortality values of asiatic rice borer were calculated. Results are summarized in Table 7.

TABLE 7

| Tested agrochemical | Concentration of agrochemical (ppm) | Rice borer mortality (%) |
|---|---|---|
| KSB-1939H$_2$ | 1 | 100 |
| | 0.2 | 90 |
| KSB-1939H$_4$ | 1 | 100 |
| | 0.2 | 90 |
| KSB-1939H$_5$ | 1 | 100 |
| | 0.2 | 90 |

Test 6 (In Vitro Test against Microfilariae)

Using the in vitro cultivation method described by K. Ando in Japan Journal of Parasitology, 29, 483 (1980), effects of KSB-1939 compounds against microfilariae of *Dirofilaria immitis* were evaluated. Each test compound was dissolved in dimethylsulfoxide to obtain an aqueous agrochemical formulation containing 5 mg/ml of the compound. The formulation was inoculated into incubation chambers to give a dimethylsulfoxide concentration not higher than 1%. The microfilariae had been collected from the venous blood of a dog with the microfilaremia. LD$_{50}$ values on the 10th day after the initiation of the incubation are given in Table 8.

TABLE 8

| Agrochemical | LD$_{50}$ (μg/ml) |
|---|---|
| KSB-1939H$_2$ | 3.40 |
| KSB-1939H$_3$ | 1.50 |
| KSB-1939H$_4$ | 3.30 |
| KSB-1939H$_5$ | 1.60 |
| KSB-1939S$_5$ | 3.50 |
| KSB-1939L$_{3\alpha\beta}$ mixture | 3.80 |
| Milbemycin D | 7.50 |

Test 7 (In Vitro Test against *Caenorhabditis elegans*)

Using the in vitro selection test described by K. G. Shimpkin and G. L. Coles in Parasitology, 79, 19 (1979), effects of KSB-1939 compounds against *Caenorhabditis elegans* were evaluated. Each test compound was dissolved in dimethylsulfoxide to obtain an aqueous agrochemical formulation containing 5 mg/ml of the compound. The evaluation was conducted by inoculating the thus-prepared formulations in test tubes to give a dimethylsulfoxide concentration not higher than 1%. 100% insecticidal effects were observed when the test compounds were contained in an amount of at least 10 μg per ml.

Test 8 (Test against Dog Nematodes)

A test was conducted using dogs which had been infected naturally with *Ancylostoma caninum* or *Toxocara canis*. Namely, using 8 hybrid dogs of 2 months old, KSB-1939H$_2$ according to this invention was administered subcutaneously at a dosage of 0.1 mg/kg-body weight or orally at a dosage of 0.5 mg/kg-body weight. Administration was effected only once. Evaluation was conducted by comparing the number of eggs contained in feces excreted from each dog before the treatment with that of eggs contained in feces excreted from the dog after the treatment. 100% activities were observed with all the dogs, irrespective of the dosage and administration route.

Test 9 (Test against Cat Nematode)

A test was conducted using cats which had been infected naturally with *Toxocara cati*. Namely, 4 hybrid cats infected with the nematode were administered with KSB-1939H$_2$ of this invention at a dosage of 0.05 mg/kg-body weight in the case of subcutaneous administration or at a dosage of 0.1 mg/kg-body weight in the case of oral administration. Evaluation was conducted by comparing the number of eggs contained in feces excreted from each cat before the treatment with that of eggs contained in feces excreted from the cat after the treatment. 100% activities were observed with all the cats, irrespective of the dosage and administration route.

Test 10 (Test against Sheep Nematode)

A test was conducted using sheep which had been infected with *Haemonchus concurtus*. Namely, KSB-1939H$_4$ of this invention was formulated into oral drenches. Four sheep which had been infected artificially with *Haemonchus concurtus* were administered with the compound by injecting the oral drenches into their rumens respectively. They were treated only once by a single dosage of 0.5 mg/kg-body weight or 1.0 mg/kg-body weight. Evaluation was conducted by comparing the number of eggs contained in feces excreted from each sheep before the treatment with that of eggs contained in feces excreted from the sheep after the treatment. 100% activities were observed with the sheep treated at the dosage of 1.0 mg/kg, while 80–90% activities were recognized with the sheep treated at the dosage of 0.5 mg/kg.

Test 11 (Acute Toxicity Test)

The acute toxicity (oral) of one of the compounds of this invention was investigated using rats (male and female, F344, 7 weeks old) and mice (male and female, B$_6$C$_3$F$_1$, 7 weeks old). Results are summarized in Tables 9A and 9B.

TABLE 9A

| Chemical | Sex | LD$_{50}$ (ppm) Rat |
|---|---|---|
| KSB-1939H$_2$ | M | >5000 |
|  | F | >5000 |
| Ivermectin* | M | 58.8 |
|  | F | 62.0 |
| Milbemycin D** | M | 1847.1 |
|  | F | 1609.5 |

*Dainippon Pharmaceutical Co., Ltd.: Data of Caldmeck Tablet Study Group.
**Journal of Japanese Veterinary Society, 39, 422–426 (1986).

TABLE 9B

| Chemical | Sex | LD$_{50}$ (ppm) Mouse |
|---|---|---|
| KSB-1939H$_2$ | M | >5000 |
|  | F | >5000 |
| KSB-1939H$_3$ | M | >5000 |
|  | F | >5000 |
| KSB-1939S$_5$ | M | >5000 |
|  | F | >5000 |
| Ivermectin | M | 58.2 |
|  | F | 59.7 |
| Milbemycin D | M | 2467.0 |

TABLE 9B-continued

| Chemical | Sex | LD$_{50}$ (ppm) Mouse |
|---|---|---|
|  | F | 2998.5 |

In the claims:

1. A process for producing a compound having the formula (I):

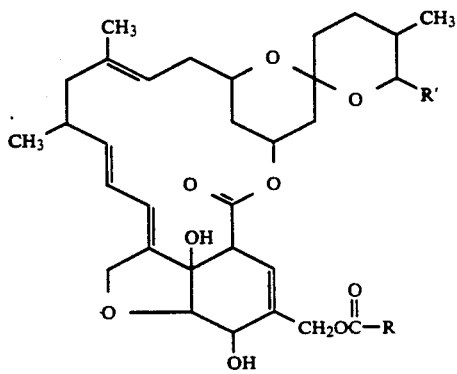

wherein R is —(CH$_2$)$_n$CH(CH$_3$)$_2$, —(CH$_2$)$_2$CH$_3$, or —CH=C(CH$_3$)(CH$_2$)$_m$CH$_3$, wherein n is an integer of 0–2 and m is an integer of 0 or 1, and R' is a methyl or ethyl group, comprising culturing *Streptomyes hygroscopicus* KSB-1939 deposited as FERM BP-1901, and mutants thereof capable of producing said compound of formula (I), and then collecting said compound from the resultant culture.

2. The process of claim 1, wherein R is —(CH$_2$)$_n$CH(CH$_3$)$_2$ or —(CH$_2$)$_2$CH$_3$.

3. The process of claim 1, wherein R is —CH=C(CH$_3$)(CH$_2$)$_m$CH$_3$.

4. The process of claim 1, wherein R' is methyl.

5. The process of claim 1, wherein R' is ethyl.

6. The process of claim 1, wherein said culturing step is conducted under aerobic conditions in a submerged tank culture.

7. The process of claim 1, wherein said culturing is conducted at a temperature in the range from 15°–37° C.

8. The process of claim 1, wherein said culturing is conducted for about 5–10 days.

9. The process of claim 1, wherein said collecting step comprises filtering or centrifuging the cultured strain to collect the cells thereof, extracting the cells with an organic solvent and then removing the organic solvents to obtain said compound.

10. The process of claim 1, wherein R' is methyl, R is CH(CH$_3$)$_2$ and n is 0.

11. The process of claim 1, wherein R' is methyl, R is CH$_2$CH$_2$CH$_3$, and n is 0.

12. The process of claim 1, wherein R' is methyl and R is CH$_2$CH$_2$CH(CH$_3$)$_2$ and n is 2.

13. The process of claim 1, wherein R' is methyl, R is CH=C(CH$_3$)$_2$ and m is 0.

* * * * *